(12) United States Patent
Schoenafinager et al.

(10) Patent No.: US 8,791,133 B2
(45) Date of Patent: Jul. 29, 2014

(54) PYRIDYLVINYLPYRAZOLOQUINOLINES AS PAR1 INHIBITORS

(71) Applicant: Sanofi, Paris (FR)

(72) Inventors: Karl Schoenafinager, Alzenau (DE); Henning Steinhagen, Schwalbach am Taunus (DE); Bodo Scheiper, Munich (DE); Uwe Heinelt, Wiesbaden (DE); Volkmar Wehner, Sandberg (DE); Matthias Herrmann, Hofheim (DE); Jacques Mauger, Oro Valley, AZ (US); Pavel Safar, Oro Valley, AZ (US)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/652,893

(22) Filed: Oct. 16, 2012

(65) Prior Publication Data
US 2013/0040981 A1 Feb. 14, 2013

Related U.S. Application Data

(63) Continuation of application No. PCT/EP2011/055964, filed on Apr. 14, 2011.

(30) Foreign Application Priority Data

Apr. 16, 2010 (EP) .................... 10305395

(51) Int. Cl.
*A61K 31/4745* (2006.01)
(52) U.S. Cl.
USPC .............. 514/293; 514/278; 546/15; 546/82
(58) Field of Classification Search
CPC ........... A61K 31/4745; A61K 31/4188; C07D 471/10
USPC ................. 514/293, 273; 546/15, 82
See application file for complete search history.

(56) References Cited

U.S. PATENT DOCUMENTS

| | | | |
|---|---|---|---|
| 6,063,847 | A | 5/2000 | Chackalamannil et al. |
| 6,326,380 | B1 | 12/2001 | Chackalamannil et al. |
| 2004/0152736 | A1 | 8/2004 | Chackalamannil et al. |
| 2004/0176418 | A1 | 9/2004 | Thiruvengadam et al. |
| 2004/0192753 | A1 | 9/2004 | Chackalamannil et al. |
| 2005/0267155 | A1 | 12/2005 | Chelliah et al. |
| 2006/0063847 | A1 | 3/2006 | Matsumura et al. |
| 2006/0079684 | A1 | 4/2006 | Chackalamannil et al. |
| 2007/0149518 | A1 | 6/2007 | Chackalamannil et al. |
| 2007/0232635 | A1 | 10/2007 | Chelliah et al. |

FOREIGN PATENT DOCUMENTS

| | | |
|---|---|---|
| EP | 1391451 | 2/2004 |
| EP | 1391452 | 2/2004 |
| WO | WO 99/26943 | 6/1999 |
| WO | WO 01/96330 | 12/2001 |
| WO | WO 03/089428 | 10/2003 |
| WO | WO 2006/076564 | 7/2006 |
| WO | WO 2006/105217 | 10/2006 |
| WO | WO 2008/042422 | 4/2008 |
| WO | WO 2009/124103 | 10/2009 |

OTHER PUBLICATIONS

U.S. Appl. No. 13/652,898, filed Oct. 16, 2012, Schoenafinger, et al.
Chackalamannil, et al., Thrombin Receptor (PAR-1) Antagonists as Novel Antithrombotic Agents, Expert Opinion on Therapeutic Patents, vol. 16, No. 4, pp. 493-505, (2006).
Chebanov, et al., Tuning of Chemo- and Regioselectivities in Multicomponent Condensations of 5-Aminopyrazoles, Dimedone, and Aldehydes, Journal of Organic Chemistry, vol. 73, No. 13, (2008), pp. 5110-5118.
Quiroga, et al., Synthesis of 4-Aryl-4,7,8,9-Tetrahydro-6H-Pyrazolo[3,4-b]Quinolin-5-Ones, Journal of Heterocyclic Chemistry, vol. 35, No. 3, pp. 575-578, (1998).
Hollenberg, et al., International Union of Pharmacology,. XXVIII. Proteinase-Activated Receptors, Pharmacological Reviews, vol. 54, No. 2, pp. 203-217, (2002).
Brass, Platelets and Proteases, Nature, vol. 413, pp. 26-27, (2001).
Chintala, et al., Efficacy of SCH 602539, A Selective Thrombin Receptor Antagonist, Alone and in Combination With Cangrelor in a Folts Model of Thrombosis in Anesthetized Monkeys, Eur. Heart J., vol. 28, (Suppl. 1), (2007), pp. 188, Abstract.
International Search Report for WO2011/128420 dated Oct. 20, 2011.

*Primary Examiner* — Savitha Rao
*Assistant Examiner* — Angela Brown-Pettigrew

(57) ABSTRACT

The disclosure relates to compounds of formula I:

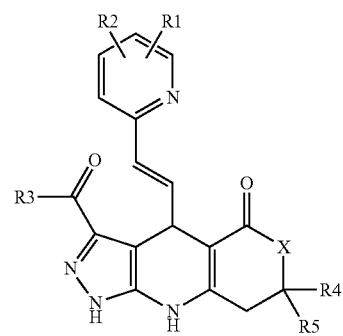

wherein the groups R1, R2, R3, R4, R5 and X are as defined in the disclosure, having antithrombotic activity, which in particular inhibits the protease-activated receptor 1 (PAR1). The disclosure further relates to methods for producing the same and to the use thereof as a pharmaceutical product.

8 Claims, No Drawings

PYRIDYLVINYLPYRAZOLOQUINOLINES AS PAR1 INHIBITORS

This application is a continuation of International Application No. PCT/EP2011/055964, filed Apr. 14, 2011, which is incorporated herein by reference in its entirety; which claims the benefit of priority of European Patent Application No. 10305395.5, filed Apr. 16, 2010.

The invention relates to novel compounds of the formula I

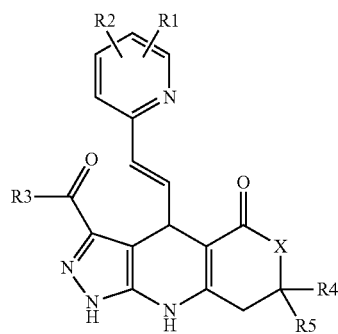

where R1, R2, R3, R4, R5 and X have the meaning defined below. The compounds of the formula I have antithrombotic activity and inhibit in particular the protease-activated receptor 1 (PAR1). The invention further relates to processes for preparing the compounds of the formula I and their use as medicaments.

The protease-activated receptor 1 (PAR1) is a thrombin receptor which belongs to the class of G protein-coupled receptors (GPCR). The gene for PAR1 is located on chromosome 5q13, consists of two exons and covers a region of about 27 kb. PAR1 is expressed inter alia in endothelial cells, smooth muscle cells, fibroblasts, neurons and human blood platelets. On blood platelets, PAR1 is an important receptor of signal transmission and is involved in initiating the aggregation of blood platelets. Activation of the PARs takes place by proteolytic elimination of part of the N terminus of the PARs, thus exposing a new N-terminal sequence which then activates the receptor (M. D. Hollenberg et al., Pharmacol. Rev. 54:203-217, 2002).

The coagulation of blood is a process for controlling blood flow which is essential for the survival of mammals. The process of coagulation and the subsequent breakup of the clot after wound healing has taken place starts after damage to a vessel and can be divided into four phases:
1. The phase of vascular constriction: the blood loss into damaged areas is reduced thereby.
2. The next phase is that of platelet adhesion to the exposed collagen in the subendothelium. This primary adhesion to the matrix activates the platelets, which then secrete various activators which lead to enhancement of the activation. These activators additionally stimulate further recruitment of new platelets to the site of vessel damage and promote platelet aggregation. The platelets aggregate at the site of vessel wall damage and form a still loose platelet plug. Activation of platelets further leads to presentation of phosphatidylserine and phosphatidylinositol along the cell membrane surfaces. Exposure of these phospholipids is essential for binding and activating the multienzyme complexes of the blood coagulation cascade.
3. The initially still loose platelet aggregate is crosslinked by fibrin. If the thrombus comprises only platelets and fibrin, it is a white thrombus. If red blood corpuscles are additionally present, it is a red thrombus.
4. After wound healing, the thrombus is broken up by the action of the protein plasmin.

Two alternative pathways lead to the formation of a fibrin clot, the intrinsic and the extrinsic pathway. These pathways are initiated by different mechanisms, but in a later phase they converge to a common pathway of the coagulation cascade. Formation of a red thrombus or a clot on the basis of a vessel wall abnormality without wound is the result of the intrinsic pathway. Fibrin clot formation as response to tissue damage or injury is the result of the extrinsic pathway. Both pathways include a relatively large number of proteins which are known as coagulation factors.

The intrinsic pathway requires coagulation factors VIII, IX, X, XI and XII and also prekallikrein, high molecular weight kininogen, calcium ions and phospholipids from platelets. Each of these proteins activates factor X. The intrinsic pathway is initiated when prekallikrein, high molecular weight kininogen, factor XI and XII bind to a negatively charged surface. This moment is referred to as the contact phase. Exposure to a vessel wall collagen is the primary stimulus of the contact phase. The result of the contact phase processes is conversion of prekallikrein into kallikrein, which in turn activates factor XII. Factor XIIa hydrolyzes further prekallikrein to kallikrein, so that the result is activation. As the activation of factor XII increases there is activation of factor XI which leads to release of bradykinin, a vasodilator. The initial phase of vasoconstriction is terminated thereby. Bradykinin is produced from the high molecular weight kininogen. In the presence of $Ca^{2+}$ ions, factor XIa activates factor IX. Factor IX is a proenzyme which contains vitamin K-dependent, γ-carboxyglutamate (GLA) residues. The serine protease activity becomes evident after $Ca^{2+}$ ions have bound to these GLA residues. Several of the serine proteases in the blood coagulation cascade (factors II, VII, IX and X) contain such vitamin K-dependent GLA residues. Factor IXa cleaves factor X and leads to activation to factor Xa. The precondition for the formation of factor IXa is the formation of a protease complex of $Ca^{2+}$ ions and factors VIIIa, IXa and X on the surface of activated platelets. One of the reactions of activated platelets is the presentation of phosphatidylserine and phosphatidylinositol along the surfaces. Exposure of these phospholipids is a precondition for the formation of the protease complex. In this process, factor VIII acts as a receptor for factors IXa and X. Factor VIII therefore represents a cofactor in the coagulation cascade. Activation of factor VIII with formation of factor VIIIa, the actual receptor, requires only a minimal amount of thrombin. As the concentration of thrombin increases, factor VIIIa is finally cleaved further, and inactivated, by thrombin. This dual activity of thrombin in relation to factor VIII leads to the protease complex formation being self-limiting and thus the blood coagulation being localized.

PAR1 and PAR4 play a central role in the activation of human blood platelets by thrombin; activation of these receptors leads to morphological changes in blood platelets, release of ADP and aggregation of the blood platelets (S. Brass, Nature 413:26-27, 2001).

PAR1 inhibitors are described for example in EP 1391451, EP 1391452, U.S. Pat. No. 6,063,847, US 2004/152736, US 2004/176418, US 2004/192753, US 2005/267155, US 2006/063847, US 2006/079684, US 2007/149518, US 2007/232635, US 6,326,380, WO 99/26943, WO 01/96330, WO 03/089428, WO 2006/076564, WO 2006/105217 and WO 2008/042422.

It has been found that the compounds of the formula I show a high specific inhibition of the protease-activated receptor 1.

Compounds of the formula I are therefore suitable for prophylactic and therapeutic use in humans suffering from disorders associated with thromboses, embolisms, hypercoagubility or fibrotic alterations. Examples of such disorders are thrombosis, deep vein thrombosis, pulmonary embolisms, cerebral infarction, myocardial infarction, high blood pressure, inflammatory disorders, rheumatism, asthma, glomerulonephritis or osteoporosis. The compounds of the formula I can be employed for secondary prevention and are suitable both for acute and for long-term therapy. The compounds of the formula I can also be employed in combination with active compounds which act by antithrombotic principles different from PAR1.

Accordingly, the invention relates to a compound of the formula I

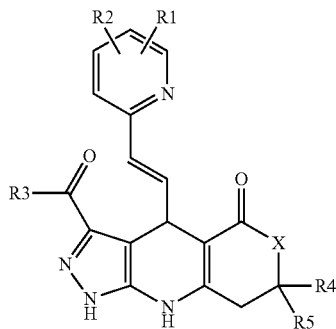

I and/or all stereoisomeric or tautomeric forms of the compound of the formula I and/or mixtures of these forms in any ratio, and/or a physiologically acceptable salt of the compound of the formula I, where R1 and R2 are identical or different and are independently of one another hydrogen, —($C_1$-$C_6$)-alkyl, —O—($C_1$-$C_6$)-alkyl, aryl, halogen or hetaryl, where alkyl, aryl and hetaryl are in each case unsubstituted or mono-, di- or trisubstituted independently of one another by F, Cl, Br, CN, —($C_1$-$C_4$)-alkyl, —O—($C_1$-$C_4$)-alkyl, —OH, —$NH_2$, —NH—($C_1$-$C_4$)-alkyl, —N(($C_1$-$C_4$)-alkyl)$_2$, —$OCF_3$, —$SCF_3$ or —$CF_3$, or R1 and R2 together with the ring atoms to which they are respectively attached form a 5- to 7-membered ring, where the ring consists only of carbon atoms, or 1, 2 or 3 of these atoms are replaced by N, O or S atoms, where the ring is unsubstituted or mono-, di- or trisubstituted independently of one another by F, Cl, Br, CN, —($C_1$-$C_4$)-alkyl, —O—($C_1$-$C_4$)-alkyl, —OH, —$NH_2$, —$OCF_3$, —$SCF_3$, —NH—($C_1$-$C_4$)-alkyl, —N(($C_1$-$C_4$)-alkyl)$_2$ or —$CF_3$;

R3 is OH, —O—($C_1$-$C_8$)-alkyl, —O—($C_1$-$C_6$)-alkylene-NH—C(O)—O—($C_1$-$C_4$)-alkyl, —O—($C_1$-$C_6$)-alkylene-$NH_2$, —$NH_2$, —NH—($C_1$-$C_8$)-alkyl, —NH—($C_1$-$C_6$)-alkylenearyl, —NH—($C_1$-$C_8$)-alkylene-O—($C_1$-$C_4$)-alkyl, —NH—($C_1$-$C_8$)-alkyl-OH, —NH—($C_1$-$C_6$)-alkylene-NH—C(O)—O—($C_1$-$C_4$)-alkyl, —NH—($C_1$-$C_6$)-alkylene-$NH_2$, —NH—($C_0$-$C_6$)-alkylene-($C_3$-$C_7$)-cycloalkyl, —NH—($C_0$-$C_6$)-alkylenehetaryl, —N(($C_1$-$C_4$)-alkyl)$_2$, or a cyclic amine which is selected from the group consisting of hexamethyleneimine, morpholine, piperazine, piperidine, pyrrolidine and thiomorpholine, and is attached via the nitrogen atom, where aryl, cycloalkyl, hetaryl and cyclic amine are in each case unsubstituted or mono-, di- or trisubstituted independently of one another by F, Cl, —OH, —($C_1$-$C_4$)-alkyl, —($C_1$-$C_4$)-alkylene-$NH_2$, —($C_1$-$C_4$)-alkylene-OH or —O—($C_1$-$C_4$)-alkyl;

R4 and R5 are identical or different and are independently of one another hydrogen, —NH—R7, —($C_1$-$C_6$)-alkyl or aryl, or R4 and R5 together with the carbon atom to which they are attached form ($C_3$-$C_7$)-cycloalkyl or a saturated or unsaturated 4- to 7-membered ring in which one or two of the carbon atoms in the ring are replaced by O, S, $SO_2$ or N—R6;

X is a covalent bond, $CH_2$, CH(($C_1$-$C_6$)-alkyl), C(($C_1$-$C_4$)-alkyl)$_2$, N—R6 or oxygen;

R6 is hydrogen, —($C_1$-$C_6$)-alkyl, —($C_1$-$C_6$)-alkylene-($C_3$-$C_7$)-cycloalkyl, —($C_1$-$C_6$)-alkylenearyl or —C(O)—O—($C_1$-$C_6$)-alkyl;

R7 is hydrogen, —($C_1$-$C_6$)-alkyl, —($C_1$-$C_6$)-alkylene-($C_3$-$C_7$)-cycloalkyl, —($C_1$-$C_6$)-alkylenearyl or —C(O)—O—($C_1$-$C_6$)-alkyl;

where the term "hetaryl" means ring systems having 4 to 15 carbon atoms which are present in one, two or three ring systems connected together, and which comprise, depending on the ring size, one, two, three or four identical or different heteroatoms from the group consisting of oxygen, nitrogen and sulfur.

The invention furthermore relates to a compound of the formula I, and/or all stereoisomeric or tautomeric forms of the compound of the formula I and/or mixtures of these forms in any ratio, and/or a physiologically acceptable salt of the compound of the formula I, where R1 and R2 are identical or different and are independently of one another hydrogen, —($C_1$-$C_6$)-alkyl, —O—($C_1$-$C_6$)-alkyl, aryl, halogen or hetaryl, where alkyl, aryl and hetaryl are in each case unsubstituted or mono-, di- or trisubstituted independently of one another by F, Cl, Br, CN, —($C_1$-$C_4$)-alkyl, —O—($C_1$-$C_4$)-alkyl or —$CF_3$, or R1 and R2 together with the ring atoms to which they are respectively attached form a 5- to 7-membered ring, where the bicyclic ring system consisting of this ring and the pyridine ring carrying R1 and R2 is selected from the group consisting of quinoline, 6,7-dihydro-5H-[1]pyridine, [1,3]dioxo[4,5-b]pyridine, furo[3,2-b]pyridine, isoquinoline, [1,7]naphthyridine, pyridopyrazine, pyrido[2,3-c]pyridazine, pyridopyridine, pyrido[2,3-d]pyrimidine, 5H-[1]pyridine, 1H-pyrrolo[2,3-b]pyridine, 6,7,8,9-tetrahydro-5H-pyrido[2,3-c]azepine, 5,6,7,8-tetrahydroquinoline and thieno[3,2-b]pyridine;

R3 is —O—($C_1$-$C_6$)-alkyl, —O—($C_1$-$C_6$)-alkylene-NH—C(O)—O—($C_1$-$C_4$)-alkyl, —O—($C_1$-$C_6$)-alkylene-$NH_2$, —NH—($C_1$-$C_6$)-alkyl, —NH—($C_1$-$C_6$)-alkylenearyl, —NH—($C_1$-$C_6$)-alkylene-($C_3$-$C_7$)-cycloalkyl, —NH—($C_1$-$C_6$)-alkylenehetaryl, —N(($C_1$-$C_4$)-alkyl)$_2$ or a cyclic amine which is selected from the group consisting of hexamethyleneimine, morpholine, piperazine, piperidine, pyrrolidine and thiomorpholine, and is attached via the nitrogen atom, where aryl, cycloalkyl, hetaryl and cyclic amine are in each case unsubstituted or mono-, di- or trisubstituted independently of one another by F, Cl, —OH, —($C_1$-$C_4$)-alkylene-$NH_2$, —($C_1$-$C_4$)-alkylene-OH or —($C_1$-$C_4$)-alkyl;

R4 and R5 are identical or different and are independently of one another hydrogen or —($C_1$-$C_6$)-alkyl, or R4 and R5 together with the carbon atom to which they are attached form ($C_3$-$C_6$)-cycloalkyl or a saturated or unsaturated 4- to 7-membered ring selected from the group consisting of azepine, azetidine, [1,4]-diazepane, [1,2]-diazepine, [1,3]-diazepine, [1,4]-diazepine, dihydroimidazolone, dioxazole, dioxazine, dioxole, [1,3]-dioxolene, [1,3]-dioxolane, furan, imidazole, imidazoline, imidazolidine, imidazolidinone, isothiazole, isothiazolidine, isothiazoline, isoxazole, isoxazoline, isoxazolidine, morpholine, oxathiazine dioxide, [1,2]-oxathiepane, [1,2]-oxathiolane, [1,4]-oxazepane, [1,2]-oxazine, [1,3]-oxazine, [1,4]-oxazine, oxazolone, oxazole, oxazolidinone, oxetane, piperazine, piperidine, pyrane, pyrazine, pyrazole, pyrazoline, pyrazolidine, pyridazine, pyridine, pyridinone, pyrimidine, pyrrole, pyrrolidine, pyrrolidinone, pyrroline, tetrahydrofuran, tetrahydropyran, tetrahydropyridine, [1,4]-thiazepanes, [1,2]-thiazine, [1,3]-thiazine, [1,4]-thiazine, [1,3]-thiazole, thiazole, thiazolidine, thiazoline, thiophene, thietane, thiomorpholine, thiophene 1,1-dioxide, thiophene 1-oxide and thiopyran 1,1-dioxide;

X is a covalent bond, $CH_2$, $CH((C_1-C_4)$-alkyl), $C((C_1-C_4)$-alkyl)$_2$, N—R6 or oxygen;

where the term "hetaryl" means ring systems having 4 to 15 carbon atoms which are present in one, two or three ring systems connected together, and which may, depending on the ring size, comprise one, two, three or four identical or different heteroatoms from the group consisting of oxygen, nitrogen and sulfur.

The invention furthermore relates to a compound of the formula I, and/or all stereoisomeric or tautomeric forms of the compound of the formula I and/or mixtures of these forms in any ratio, and/or a physiologically acceptable salt of the compound of the formula Ia,

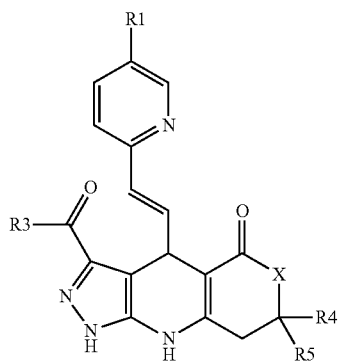

Ia where
R1 is hydrogen, —$(C_1-C_4)$-alkyl, phenyl, Cl, Br or hetaryl, where hetaryl is selected from the group consisting of acridinyl, azepinyl, azetidinyl, aziridinyl, benzimidazolyl, benzofuranyl, benzothiofuranyl, benzothiophenyl, benzoxazolyl, benzthiazolyl, benztriazolyl, benzisoxazolyl, benzisothiazolyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, deca-hydroquinolinyl, dibenzofuranyl, dibenzothiophenyl, dihydrofuran[2,3-b]-tetrahydrofuranyl, dihydrofuranyl, dioxolyl, dioxanyl, 2H, 6H-1,5,2-dithiazinyl, furanyl, furazanyl, imidazolidinyl, imidazolinyl, imidazolyl, 1H-indazolyl, indolinyl, indolizinyl, indolyl, 3H-indolyl, isobenzofuranyl, isoquinolinyl, isochromanyl, isoindazolyl, isoindolinyl, isoindolyl, isothiazolidinyl, 2-isothiazolinyl, isothiazolyl, isoxazolyl, isoxazolidinyl, 2-isoxazolinyl, morpholinyl, naphthyridinyl, octahydroisoquinolinyl, 1,2,3-oxadiazolyl, 1,2,4-oxadiazolyl, 1,2,5-oxadiazolyl, 1,3,4-oxadiazolyl, oxazolidinyl, oxazolyl, oxetanyl, oxothiolanyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pyridooxazolyl, pyridoimidazolyl, pyridothiazolyl, pyridothiophenyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyranyl, tetrahydropyridinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolidinyl, thiazolinyl, thiazolyl, thienyl, thienoimidazolyl, thienooxazolyl, thienopyrrole, thienopyridine, thienothiazolyl, thienothiophenyl, thiomorpholinyl, triazinyl, 1,2,3-triazolyl, 1,2,4-triazolyl, 1,2,5-triazolyl, 1,3,4-triazolyl and xanthenyl, and where phenyl and hetaryl are in each case unsubstituted or mono- or disubstituted independently of one another by F, Br, Cl, CN, —$(C_1-C_4)$-alkyl, —O—$(C_1-C_4)$-alkyl or —$CF_3$;

R3 is OH, —O—$(C_1-C_6)$-alkyl, —O—$(C_1-C_6)$-alkylene-NH—C(O)—O—$(C_1-C_4)$-alkyl, —O—$(C_1-C_6)$-alkylene-$NH_2$, —NH—$(C_1-C_4)$-alkyl, —NH-benzyl or —NH-methylene-$(C_3-C_6)$-cycloalkyl, where cycloalkyl is unsubstituted or monosubstituted by —$(C_1-C_4)$-alkyl, —$(C_1-C_4)$-alkylene-$NH_2$ or —$CH_2$—OH;

R4 and R5 are identical or different and are independently of one another hydrogen or —$(C_1-C_4)$-alkyl, or R4 and R5 together with the carbon atom to which they are attached form cyclopropyl, cyclobutyl, cyclopentyl or cyclohexyl;

X is a covalent bond, $CH_2$, $C((C_1-C_4)$-alkyl)$_2$ or oxygen.

The invention furthermore relates to a compound of the formula Ia, and/or all stereoisomeric or tautomeric forms of the compound of the formula Ia and/or mixtures of these forms in any ratio, and/or a physiologically acceptable salt of the compound of the formula Ia, where R1 is —$(C_1-C_4)$-alkyl, phenyl, Cl or Br, where phenyl is unsubstituted or mono-, di- or trisubstituted independently of one another by F, Cl, Br, CN, —$(C_1-C_4)$-alkyl, —O—$(C_1-C_4)$-alkyl or —$CF_3$;

R3 is OH, —O—$(C_1-C_4)$-alkyl, —O—$(C_1-C_6)$-alkylene-NH—C(O)—O—$(C_1-C_4)$-alkyl, —O—$(C_1-C_6)$-alkylene-$NH_2$, —NH—$(C_1-C_3)$-alkyl or —NH-methylene-$(C_3-C_6)$-cycloalkyl, where cycloalkyl is unsubstituted or monosubstituted by —$(C_1-C_4)$-alkyl, —$(C_1-C_4)$-alkylene-$NH_2$ or —$CH_2$—OH;

R4 and R5 are identical or different and are independently of one another hydrogen or —$(C_1-C_4)$-alkyl, or R4 and R5 together with the carbon atom to which they are attached form cyclobutyl or cyclopentyl;

X is a covalent bond, $CH_2$, $C((C_1-C_4)$-alkyl)$_2$ or oxygen.

The invention furthermore relates to a compound of the formula I or Ia, and/or all stereoisomeric or tautomeric forms of the compound of the formula I or Ia and/or mixtures of these forms in any ratio, and/or a physiologically acceptable salt of the compound of the formula I or Ia, selected from the following compounds:

4-{(E)-2-[5-(3-fluorophenyl)pyridin-2-yl]vinyl}-7,7-dimethyl-5-oxo-4,5,6,7,8,9-hexahydro-1H-pyrazolo[3,4-b]quinoline-3-cyclopropylmethylcarboxamide, 7,7-dimethyl-4-[(E)-2-(6-methylpyridin-2-yl)vinyl]-5-oxo-4,5,6,7,8,9-hexahydro-1H-pyrazolo[3,4-b]quinoline-3-isopropylcarboxamide, 4-{(E)-2-[5-(3-fluorophenyl)pyridin-2-yl]vinyl}-7,7-dimethyl-5-oxo-4,5,6,7,8,9-hexahydro-1H-pyrazolo[3,4-b]quinoline-3-isopropylcarboxamide, 4-{(E)-2-[5-(3-fluorophenyl)pyridin-2-yl]vinyl}-6,6-dimethyl-5-oxo-4,5,6,7,8,9-hexahydro-1H-pyrazolo[3,4-b]quinoline-3-cyclopropylmethylcarboxamide, 4-{(E)-2-[5-(3-fluorophenyl)pyridin-2-yl]vinyl}-7-isopropyl-5-oxo-4,5,6,7,8,9-hexahydro-1H-pyrazolo[3,4-b]quinoline-3-cyclopropylmethylcarboxamide, 4-[(E)-2-(5-bromopyridin-2-yl)vinyl]-7,7-dimethyl-5-oxo-4,5,6,7,8,9-hexahydro-1H-pyrazolo[3,4-b]quinoline-3-cyclopropylmethylcarboxamide, 4-[(E)-2-(5-bromopyridin-2-yl)vinyl]-7,7-dimethyl-5-oxo-4,5,6,7,8,9-hexahydro-1H-pyrazolo[3,4-b]quinoline-3-isopropylcarboxamide, 4-{(E)-2-[5-(3-fluorophenyl)pyridin-2-yl]vinyl}-7-methyl-5-oxo-4,5,6,7,8,9-hexahydro-1H-pyrazolo[3,4-b]quinoline-3-isopropylcarboxamide, 4-{(E)-2-[5-(3-fluorophenyl)pyridin-2-yl]vinyl}-7-methyl-5-oxo-4,5,6,7,8,9-hexahydro-1H-pyrazolo[3,4-b]quinoline-3-cyclopropylmethylcarboxamide, ethyl 4-{(E)-2-[5-(3-fluorophenyl)pyridin-2-yl]vinyl}-7,7-dimethyl-5-oxo-4,5,6,7,8,9-hexahydro-1H-pyrazolo[3,4-b]quinoline-3-carboxylate, and 4-{(E)-2-[5-(3-fluorophenyl)pyridin-2-yl]vinyl}-7,7-dimethyl-5-oxo-4,5,6,7,8,9-hexahydro-1H-pyrazolo[3,4-b]quinoline-3-(2,2-dimethylpropyl)carboxamide.

The terms "alkyl", "—$(C_1-C_6)$-alkyl" and "—$(C_1-C_4)$-alkyl" mean hydrocarbon radicals whose carbon chain is straight-chain or branched and which comprise 1, 2, 3, 4, 5 or 6 carbon atoms and 1, 2, 3 or 4 carbon atoms, respectively, for example methyl, ethyl, propyl, isopropyl, butyl, isobutyl, sec-butyl, tert-butyl, pentyl, isopentyl, neopentyl, 1-ethylpropyl, hexyl, 2,3-dimethylbutyl or neohexyl. Preferably, —$(C_1-C_6)$-alkyl comprises 1 to 4 carbon atoms. "—$C_0$-Alkylene" is a covalent bond. The term "covalent bond" means a form of the chemical bond and as such is responsible for the fixed cohesion of atoms in many chemical compounds. Covalent bonds are formed particularly between the atoms of nonmetals.

The terms "—O-alkyl", "—O—$(C_1-C_6)$-alkyl" and "—O—$(C_1-C_4)$-alkyl" mean alkoxy radicals whose carbon chain is straight-chain or branched and comprise 1, 2, 3, 4, 5 or 6 carbon atoms and 1, 2, 3 or 4 carbon atoms, respectively, such as methoxy, ethoxy, propoxy, isopropoxy, butoxy, isobutoxy, tert-butoxy, 1-pentoxy, 2-pentoxy, 3-pentoxy, 1-hexoxy, 2-hexoxy or 3-hexoxy. Preferably, —O—$(C_1-C_6)$-alkyl comprises 1 to 4 carbon atoms.

The term "—$(C_3-C_7)$-cycloalkyl" means 3- to 7-membered monocycles such as cyclopropyl, cyclobutyl, cyclopentyl, cyclohexyl or cycloheptyl, the term "—$(C_3-C_6)$-cycloalkyl" means 3- to 6-membered monocycles such as cyclopropyl, cyclobutyl, cyclopentyl or cyclohexyl.

The term "aryl" means aromatic hydrocarbon radicals having 6 to 14 carbon atoms in the ring. Examples of aryl radicals are phenyl, naphthyl, for example 1-naphthyl, 2-naphthyl, anthryl or fluorenyl. Phenyl radicals and naphthyl radicals and, in particular phenyl radicals, are preferred aryl radicals.

The term "hetaryl" means ring systems having 4 to 15 carbon atoms which are present in one, two or three ring systems connected together and which comprise, depending on the ring size, one, two, three or four identical or different heteroatoms from the group consisting of oxygen, nitrogen or sulfur. Examples of these ring systems are the radicals acridinyl, azepinyl, azetidinyl, aziridinyl, benzimidazolyl, benzofuranyl, benzothiofuranyl, benzothiophenyl, benzoxazolyl, benzthiazolyl, benztriazolyl, benzisoxazolyl, benzisothiazolyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, deca-hydroquinolinyl, dibenzofuranyl, dibenzothiophenyl, dihydrofuran[2,3-b]-tetrahydrofuranyl, dihydrofuranyl, dioxolyl, dioxanyl, 2H,6H-1,5,2-dithiazinyl, furanyl, furazanyl, imidazolidinyl, imidazolinyl, imidazolyl, 1H-indazolyl, indolinyl, indolizinyl, indolyl, 3H-indolyl, isobenzofuranyl, isoquinolinyl, isochromanyl, isoindazolyl, isoindolinyl, isoindolyl, isothiazolidinyl, 2-isothiazolinyl, isothiazolyl, isoxazolyl, isoxazolidinyl, 2-isoxazolinyl, morpholinyl, naphthyridinyl, octahydroisoquinolinyl, 1,2,3-oxadiazolyl, 1,2,4-oxadiazolyl, 1,2,5-oxadiazolyl, 1,3,4-oxadiazolyl, oxazolidinyl, oxazolyl, oxetanyl, oxothiolanyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pyridooxazolyl, pyridoimidazolyl, pyridothiazolyl, pyridothiophenyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyranyl, tetrahydropyridinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolidinyl, thiazolinyl, thiazolyl, thienyl, thienoimidazolyl, thienooxazolyl, thienopyrrolyl, thienopyridinyl, thienothiazolyl, thienothiophenyl, thiomorpholinyl, triazinyl, 1,2,3-triazolyl, 1,2,4-triazolyl, 1,2,5-triazolyl, 1,3,4-triazolyl or xanthenyl.

The term "R1 and R2 together with the ring atoms to which they are respectively attached form a 5- to 7-membered ring, where the ring consists only of carbon atoms, or 1, 2 or 3 of these atoms are replaced by N, O or S atoms" means for example the following bicyclic ring systems which consist of said ring and the pyridine ring bearing R1 and R2: quinoline, 6,7-dihydro-5H-[1]pyridine, [1,3]dioxo[4,5-b]pyridine, furo[3,2-b]pyridine, isoquinoline, [1,7]naphthyridine, pyridopyrazines, pyrido[2,3-c]pyridazine, pyridopyridines, pyrido[2,3-d]pyrimidine, 5H-[1]pyridine, 1H-pyrrolo[2,3-b]pyridine, 6,7,8,9-tetrahydro-5H-pyrido[2,3-c]azepine, 5,6,7,8-tetrahydroquinoline or thieno[3,2-b]pyridine.

The term "R3 and R4 together with the ring atom to which they are both attached form a saturated or unsaturated 4- to 7-membered ring in which one or two of the carbon atoms in the ring are replaced by O, S, $SO_2$ or N—R6" means ring systems such as azepine, azetidine, [1,4]-diazepanes, [1,2]-diazepine, [1,3]-diazepine, [1,4]-diazepine, dihydroimidazolone, dioxazole, dioxazine, dioxole, [1,3]-dioxolene, [1,3]-dioxolane, furan, imidazole, imidazoline, imidazolidine, imidazolidinone, isothiazole, isothiazolidine, isothiazoline, isoxazole, isoxazoline, isoxazolidine, morpholine, oxathiazine dioxide, [1,2]-oxathiepanes, [1,2]-oxathiolanes, [1,4]-oxazepanes, [1,2]-oxazine, [1,3]-oxazine, [1,4]-oxazine, oxazolone, oxazole, oxazolidinone, oxetane, piperazine, piperidine, pyrane, pyrazines, pyrazole, pyrazoline, pyrazolidine, pyridazine, pyridine, pyridinone, pyrimidine, pyrrole, pyrrolidine, pyrrolidinone, pyrroline, tetrahydrofuran, tetrahydropyran, tetrahydropyridine, [1,4]-thiazepanes, [1,2]-thiazine, [1,3]-thiazine, [1,4]-thiazine, [1,3]-thiazole, thiazole, thiazolidine, thiazoline, thiophene, thietane, thiomorpholine, thiophene 1,1-dioxide, thiophene 1-oxide or thiopyran 1,1-dioxide.

The term "halogen" means fluorine, chlorine, bromine or iodine, preferably fluorine, chlorine or bromine, in particular fluorine or chlorine.

The term "X is a covalent bond" means the following component ring of the formula I or Ia:

The term "X is CH$_2$" means the following component ring of the formula I or Ia:

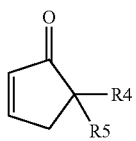

The term "X is CH(($C_1$-$C_6$)-alkyl)" means the following component ring of the formula I or Ia in which Y is —($C_1$-$C_6$)-alkyl:

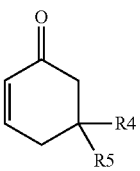

The term "X is C(($C_1$-$C_4$)-alkyl)$_2$" means the following component ring of the formula I or Ia in which Y is —(($C_1$-$C_4$)-alkyl)$_2$:

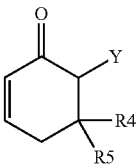

which may also be represented by the formula below in which the two groups Y are each —($C_1$-$C_4$)-alkyl).

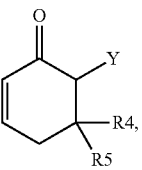

The term "X is N—R6" means the following component ring of the formula I or Ia:

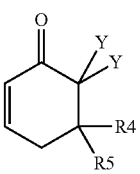

The term "X is O", that is "X is oxygen or an oxygen atom", means the following component ring of the formula I or Ia:

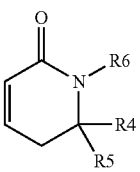

Functional groups in the compounds of the formulae I and Ia and the intermediates used for their preparation, for example amino or carboxyl groups can be masked by suitable protective groups. Suitable protective groups for amino functions are for example the t-butoxycarbonyl, the benzyloxycarbonyl or the phthaloyl group and the trityl or tosyl protective group. Suitable protective groups for the carboxyl function are for example alkyl, aryl or arylalkyl esters. Protective groups can be introduced and removed by techniques which are well known or described herein (see Greene, T. W., Wuts, P. G. M., Protective Groups in Organic Synthesis (1999), 3rd Ed., Wiley-Interscience; or Kocienski, P. J., Protecting Groups (2004), 3rd Ed., Thieme Verlag). The term protective group may also include corresponding polymer-bound protective groups.

In one embodiment of the invention, R1 and R2 in the compounds of the formula I are identical or different and are independently of one another hydrogen, —($C_1$-$C_6$)-alkyl, —O—($C_1$-$C_6$)-alkyl, aryl, halogen or hetaryl, where alkyl, aryl and hetaryl are in each case unsubstituted or mono-, di- or trisubstituted independently of one another by F, Cl, Br, CN, —($C_1$-$C_4$)-alkyl, —O—($C_1$-$C_4$)-alkyl, —OH, —NH$_2$, —NH—($C_1$-$C_4$)-alkyl, —N(($C_1$-$C_4$)-alkyl)$_2$, —OCF$_3$, —SCF$_3$ or —CF$_3$. In another embodiment, R1 and R2 in the compounds of the formula I are identical or different and are independently of one another hydrogen, —($C_1$-$C_6$)-alkyl, —O—($C_1$-$C_6$)-alkyl, aryl, halogen or hetaryl, where aryl and hetaryl are in each case unsubstituted or mono-, di- or trisubstituted independently of one another by F, Cl, Br, CN, —($C_1$-$C_4$)-alkyl, —O—($C_1$-$C_4$)-alkyl, —OH, —NH$_2$, —NH—($C_1$-$C_4$)-alkyl, —N(($C_1$-$C_4$)-alkyl)$_2$, —OCF$_3$, —SCF$_3$ or —CF$_3$. In another embodiment, R1 and R2 in the compounds of the formula I are identical or different and are independently of one another hydrogen, —($C_1$-$C_6$)-alkyl, —O—($C_1$-$C_6$)-alkyl, aryl, halogen or hetaryl, where aryl and hetaryl are in each case unsubstituted or mono-, di- or trisubstituted independently of one another by F, Cl, Br, —($C_1$-$C_4$)-alkyl, —O—($C_1$-$C_4$)-alkyl, —OCF$_3$ or —CF$_3$. In another embodiment, R1 and R2 in the compounds of the formula I are identical or different and are independently of one another hydrogen, —($C_1$-$C_6$)-alkyl, —O—($C_1$-$C_6$)-alkyl, aryl, halogen or hetaryl, where aryl and hetaryl are in each case unsubstituted or mono-, di- or trisubstituted independently of one another by F, Cl, Br, —($C_1$-$C_4$)-alkyl or —CF$_3$. In another embodiment, R1 and R2 in the compounds of the formula I are identical or different and are independently of one another hydrogen, —($C_1$-$C_6$)-alkyl, aryl, halogen or hetaryl, where aryl and hetaryl are in each case unsubstituted or mono-, di- or trisubstituted independently of one another by F, Cl, Br, —($C_1$-$C_4$)-alkyl or —CF$_3$. In another embodiment, R1 and R2 in the compounds of the formula I are identical or different and are independently of one another hydrogen, —($C_1$-$C_6$)-alkyl, phenyl or halogen, where phenyl is unsubstituted or mono-, di- or trisubstituted independently of one another by F, Cl, Br, —($C_1$-$C_4$)-alkyl or —CF$_3$.

In one embodiment of the invention, one of the groups R1 and R2 in the compounds of the formula I is hydrogen, —($C_1$-$C_6$)-alkyl, —O—($C_1$-$C_6$)-alkyl or halogen, in another embodiment, it is hydrogen, —($C_1$-$C_6$)-alkyl or halogen, in another embodiment, it is hydrogen or halogen, and in one

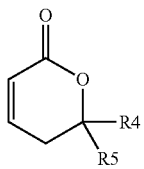

embodiment the other group R1 or R2 is —($C_1$-$C_6$)-alkyl, —O—($C_1$-$C_6$)-alkyl, aryl or hetaryl, in another embodiment, it is —($C_1$-$C_6$)-alkyl, aryl or hetaryl, in another embodiment, it is aryl or hetaryl, in another embodiment, it is phenyl, wherein in one embodiment the alkyl, —O-alkyl, aryl, phenyl or hetaryl representing the other group R1 or R2 is in each case unsubstituted or mono-, di- or trisubstituted independently of one another by F, Cl, Br, CN, —($C_1$-$C_4$)-alkyl, —O—($C_1$-$C_4$)-alkyl, —OH, —$NH_2$, —NH—($C_1$-$C_4$)-alkyl, —N(($C_1$-$C_4$)-alkyl)$_2$, —$OCF_3$, —$SCF_3$ or —$CF_3$, in another embodiment unsubstituted or mono-, di- or trisubstituted independently of one another by F, Cl, Br, —($C_1$-$C_4$)-alkyl, —O—($C_1$-$C_4$)-alkyl, —$OCF_3$ or —$CF_3$, in another embodiment unsubstituted or mono-, di- or trisubstituted independently of one another by F, Cl, Br, —($C_1$-$C_4$)-alkyl or —$CF_3$, in another embodiment unsubstituted or mono-, di- or trisubstituted independently of one another by F, Cl, Br or —($C_1$-$C_4$)-alkyl. In one embodiment of the invention, substituted groups representing R1 or R2 are substituted by one or two of the substituents listed, which can be identical or different.

In one embodiment of the invention, R1 in the compounds of the formula Ia is phenyl or hetaryl, where hetaryl has one or more of the specific meanings of hetaryl in the definition of the compounds of the formula Ia, in another embodiment, R1 is phenyl, where in one embodiment phenyl and hetaryl are in each case unsubstituted or mono- or disubstituted independently of one another by F, Cl, Br, CN, ($C_1$-$C_4$)-alkyl, —O—($C_1$-$C_4$)-alkyl or —$CF_3$, in another embodiment in each case unsubstituted or mono- or disubstituted independently of one another by F, Cl, Br, ($C_1$-$C_4$)-alkyl or —$CF_3$, and in another embodiment in each case unsubstituted or mono- or disubstituted independently of one another by F, Cl, Br, or ($C_1$-$C_4$)-alkyl.

In one embodiment of the invention, R3 in the compounds of the formula I is —OH, —O—($C_1$-$C_8$)-alkyl, —O—($C_1$-$C_6$)-alkylene-NH—C(O)—O—($C_1$-$C_4$)-alkyl, —O—($C_1$-$C_6$)-alkylene-$NH_2$, —$NH_2$, —NH—($C_1$-$C_8$)-alkyl, —NH—($C_1$-$C_6$)-alkylenearyl, —NH—($C_1$-$C_8$)-alkylene-O—($C_1$-$C_4$)-alkyl, —NH—($C_1$-$C_8$)-alkyl-OH, —NH—($C_1$-$C_6$)-alkylene-NH—C(O)—O—($C_1$-$C_4$)-alkyl, —NH—($C_1$-$C_6$)-alkylene-$NH_2$, —NH—($C_0$-$C_6$)-alkylene-($C_3$-$C_7$)-cycloalkyl, —NH—($C_0$-$C_6$)-alkylenehetaryl or —N(($C_1$-$C_4$)-alkyl)$_2$, in another embodiment, it is —OH, —O—($C_1$-$C_8$)-alkyl, —$NH_2$, —NH—($C_1$-$C_8$)-alkyl, —NH—($C_1$-$C_6$)-alkylenearyl, —NH—($C_1$-$C_8$)-alkylene-O—($C_1$-$C_4$)-alkyl, —NH—($C_1$-$C_8$)-alkyl-OH, —NH—($C_1$-$C_6$)-alkylene-NH—C(O)—O—($C_1$-$C_4$)-alkyl, —NH—($C_1$-$C_6$)-alkylene-$NH_2$, —NH—($C_0$-$C_6$)-alkylene-($C_3$-$C_7$)-cycloalkyl or —NH—($C_0$-$C_6$)-alkylenehetaryl, in another embodiment, it is —NH—($C_1$-$C_8$)-alkyl, —NH—($C_1$-$C_6$)-alkylenearyl, —NH—($C_1$-$C_8$)-alkylene-O—($C_1$-$C_4$)-alkyl, —NH—($C_1$-$C_8$)-alkyl-OH, —NH—($C_1$-$C_6$)-alkylene-NH—C(O)—O—($C_1$-$C_4$)-alkyl, —NH—($C_1$-$C_6$)-alkylene-$NH_2$, —NH—($C_0$-$C_6$)-alkylene-($C_3$-$C_7$)-cycloalkyl or —NH—($C_0$-$C_6$)-alkylenehetaryl, where aryl, cycloalkyl and hetaryl are in each case unsubstituted or mono-, di- or trisubstituted independently of one another by F, Cl, —OH, —($C_1$-$C_4$)-alkyl, —($C_1$-$C_4$)-alkylene-$NH_2$, —($C_1$-$C_4$)-alkylene-OH or —O—($C_1$-$C_4$)-alkyl. In one embodiment, hetaryl which is present in R3 in compounds of the formula I has one or more of the specific meanings which hetaryl may have in the compounds of the formula I.

In one embodiment, R3 in the compounds of the formula Ia is —OH, —O—($C_1$-$C_6$)-alkyl, —NH—($C_1$-$C_4$)-alkyl, —NH-benzyl or —NH-methylene-($C_3$-$C_6$)-cycloalkyl, in another embodiment, it is —NH—($C_1$-$C_4$)-alkyl, —NH-benzyl or —NH-methylene-($C_3$-$C_6$)-cycloalkyl, where cycloalkyl is unsubstituted or monosubstituted by —($C_1$-$C_4$)-alkyl, —($C_1$-$C_4$)-alkylene-$NH_2$ or —$CH_2$—OH.

In one embodiment of the invention, R4 and R5 in the compounds of the formula I are identical or different and are independently of one another hydrogen or —($C_1$-$C_6$)-alkyl, or R4 and R5 together with the carbon atom to which they are attached form ($C_3$-$C_7$)-cycloalkyl, i.e. a 3-membered to 7-membered cycloalkane ring which is spirocyclically attached to the ring containing group X. In another embodiment, R4 and R5 are identical or different and are independently of one another hydrogen or —($C_1$-$C_6$)-alkyl, or R4 and R5 together with the carbon atom to which they are attached form ($C_3$-$C_6$)-cycloalkyl. In another embodiment, R4 and R5 are identical or different and are independently of one another hydrogen or —($C_1$-$C_4$)-alkyl, or R4 and R5 together with the carbon atom to which they are attached form cyclobutyl or cyclopentyl, i.e. a cyclobutane ring or cyclopentane ring which is spirocyclically attached to the ring containing group X. In one embodiment of the invention, R4 and R5 in the compounds of the formula I are identical or different and are independently of one another —($C_1$-$C_6$)-alkyl, or R4 and R5 together with the carbon atom to which they are attached form ($C_3$-$C_7$)-cycloalkyl. In another embodiment, R4 and R5 are identical or different and are independently of one another —($C_1$-$C_6$)-alkyl, or R4 and R5 together with the carbon atom to which they are attached form ($C_3$-$C_6$)-cycloalkyl. In another embodiment, R4 and R5 are identical or different and are independently of one another —($C_1$-$C_4$)-alkyl, or R4 and R5 together with the carbon atom to which they are attached form cyclobutyl or cyclopentyl. In one embodiment of the invention, R4 and R5 in the compounds of the formula I together with the carbon atom to which they are attached form ($C_3$-$C_7$)-cycloalkyl, in another embodiment ($C_3$-$C_6$)-cycloalkyl, in another embodiment cyclobutyl or cyclopentyl, in another embodiment cyclopentyl.

In one embodiment of the invention, R4 and R5 in the compounds of the formula Ia are identical or different and are independently of one another hydrogen or —($C_1$-$C_4$)-alkyl, or R4 and R5 together with the carbon atom to which they are attached form cyclobutyl, cyclopentyl or cyclohexyl, i.e. a cyclobutane ring, cyclopentane ring or cyclohexane ring which is spirocyclically attached to the ring containing group X. In another embodiment, R4 and R5 are identical or different and are independently of one another hydrogen or —($C_1$-$C_4$)-alkyl, or R4 and R5 together with the carbon atom to which they are attached form cyclobutyl or cyclopentyl. In one embodiment of the invention, R4 and R5 in the compounds of the formula Ia are identical or different and are independently of one another —($C_1$-$C_4$)-alkyl, or R4 and R5 together with the carbon atom to which they are attached form cyclobutyl, cyclopentyl or cyclohexyl. In another embodiment, R4 and R5 are identical or different and are independently of one another —($C_1$-$C_4$)-alkyl, or R4 and R5 together with the carbon atom to which they are attached form cyclobutyl or cyclopentyl. In one embodiment of the invention, R4 and R5 in the compounds of the formula Ia together with the carbon atom to which they are attached form cyclopropyl, cyclobutyl, cyclopentyl or cyclohexyl, in another embodiment cyclobutyl, cyclopentyl or cyclohexyl, in another embodiment cyclobutyl or cyclopentyl, in another embodiment cyclopentyl.

In one embodiment of the invention, X in the compounds of the formula I is a covalent bond, $CH_2$, $CH((C_1\text{-}C_6)\text{-alkyl})$ or $C((C_1\text{-}C_4)\text{-alkyl})_2$, in another embodiment, it is $CH_2$, $CH((C_1\text{-}C_6)\text{-alkyl})$ or $C((C_1\text{-}C_4)\text{-alkyl})_2$, in another embodiment, it is $CH_2$ or $C((C_1\text{-}C_4)\text{-alkyl})_2$, in another embodiment, it is $CH_2$, in another embodiment, it is $C((C_1\text{-}C_4)\text{-alkyl})_2$.

In one embodiment of the invention, X in the compounds of the formula Ia is a covalent bond, $CH_2$ or $C((C_1\text{-}C_4)\text{-alkyl})_2$, in another embodiment, it is $CH_2$ or $C((C_1\text{-}C_4)\text{-alkyl})_2$, in another embodiment, it is $CH_2$, in another embodiment, it is $C((C_1\text{-}C_4)\text{-alkyl})_2$.

In one embodiment of the invention, R6 in the compounds of the formula I is hydrogen or $-(C_1\text{-}C_6)$-alkyl, in another embodiment, it is hydrogen, in another embodiment, it is $-(C_1\text{-}C_6)$-alkyl.

In one embodiment of the invention, R7 in the compounds of the formula I is hydrogen or $-(C_1\text{-}C_6)$-alkyl, in another embodiment, it is hydrogen, in another embodiment, it is $-(C_1\text{-}C_6)$-alkyl.

The invention relates to all combinations of definitions of the compounds of the formulae I and Ia and one or more of the respective embodiments described, and also to all combinations of definitions of the compounds of the formulae I and Ia and one or more of the respective embodiments described and/or one or more of the specific meanings described which a group in the compounds of the formulae I and Ia may have.

The compounds of the invention can be prepared by well known processes or by processes described herein. The invention also relates to a process for preparing a compound of the formula I or Ia and/or a stereoisomeric or tautomeric form of the compound of the formula I or Ia and/or a physiologically tolerated salt of the compound of the formula I or Ia which allows the preparation of the compounds of the formulae I and Ia, their stereoisomeric or tautomeric forms or their physiologically acceptable salts and which comprises a) reacting a compound of the formula II,

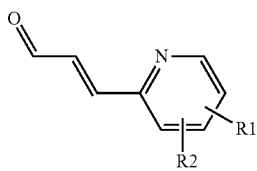

II where the radicals R1 and R2 are as defined in formula I or Ia, with a compound of the formula III and a compound of the formula IV,

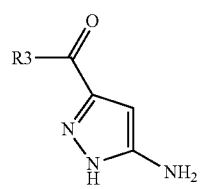

III

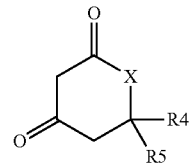

IV where the radicals R1 and R2 are as defined in formula I or Ia, in the presence of a suitable solvent or solvent mixture at 20° C. to 120° C. to give a compound of the formula I or Ia; or b) reacting a compound of the formula V,

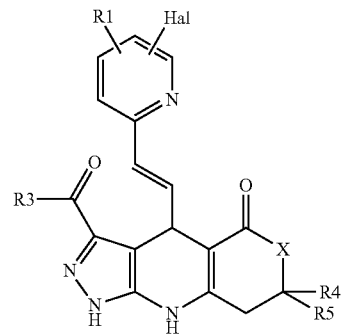

V where the radicals X, R1, R3, R4 and R5 are as defined in formula I or Ia, and Hal has the meaning of chlorine, bromine, iodine or triflate (trifluoromethanesulfonyloxy), with a compound of the formula $R2\text{-}B(OH)_2$ or a derivative thereof in the presence of a base and of a suitable metal catalyst in a suitable solvent or solvent mixture to give a compound of the formula I or Ia; or c) reacting a compound of the formula I in which X has the meaning of NH with a suitable alkylating agent in the presence of a base and in a suitable inert solvent or solvent mixture at room temperature or at elevated temperature to give a compound of the formula I in which X has the meaning of N—R6 and R6 is $-(C_1\text{-}C_6)$-alkyl, $-(C_1\text{-}C_6)$-alkylene-$(C_3\text{-}C_7)$-cycloalkyl or $-(C_1\text{-}C_6)$-alkylenearyl; or d) converting a compound of the formula I or Ia in which R3 is —OH, —O-aryl or —O—$(C_1\text{-}C_6)$-alkyl and R1, R2, R4, R5 and X are as defined in formula I or Ia by conventional processes into a compound of the formula I or Ia in which R3 is —$NH_2$, —NH—$(C_1\text{-}C_6)$-alkyl, —NH—$(C_1\text{-}C_6)$-alkylene-aryl, —NH—$(C_1\text{-}C_6)$-alkylene-$(C_3\text{-}C_7)$-cycloalkyl, —NH—$(C_1\text{-}C_6)$-alkylenehetaryl, —$N((C_1\text{-}C_4)\text{-alkyl})_2$ or a cyclic amine which is selected from the group consisting of hexamethyleneimine, morpholine, piperazine, piperidine, pyrrolidine and thiomorpholine, and is attached via the nitrogen atom, where aryl, hetaryl and cyclic amine are in each case unsubstituted or mono-, di- or trisubstituted independently of one another by F, Cl, —OH, —$(C_1\text{-}C_4)$-alkyl, —O—$(C_1\text{-}C_4)$-alkyl, aryl or hetaryl; or e) fractionating the compound of the formula I or Ia which has been prepared by processes a) to d), or a suitable precursor of the compound of the formula I or Ia which, owing to its chemical structure, occurs in enantiomeric or diastereomeric forms, by salt formation with enantiopure acids or bases, chromatography on chiral stationary phases or derivatization by means of chiral enantiopure compounds such as amino acids, separation of the diastereomers obtained in this way, and elimination of the chiral auxiliary groups, into the pure enantiomers or diastereomers; or f) either isolating the compound of the formula I or Ia prepared by processes a) to e) in free form or liberating it from a non-physiologically acceptable salt or, in the case where acidic or basic groups are present, converting it into a physiologically acceptable salt.

The compounds of the formula II can be prepared by reacting an aldehyde of the formula VI with a compound of the formula VII

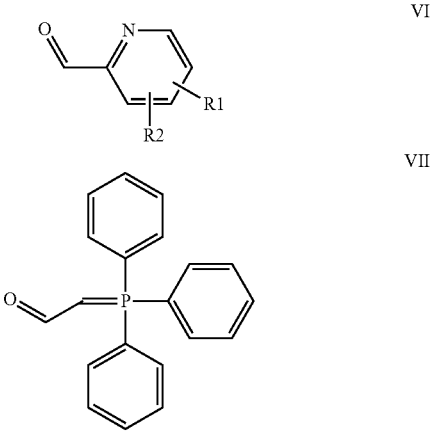

or another suitable phosphorylide reagents in a suitable solvent and, where appropriate, at elevated temperature. Aldehydes of the formula VI are either commercially available or can be prepared by known processes. Thus, for example, halogen-substituted pyridine-2-aldehydes can be reacted in the presence of suitable transition metal catalysts such as palladium or nickel and their phosphane complexes with alkyl-, aryl- and hetarylboric acid derivatives or corresponding boric ester derivatives to give alkyl, aryl and hetaryl substituted derivatives of the formula VI.

Acidic or basic compounds of the formula I or Ia may be in the form of their salts or in free form. Pharmacologically acceptable salts are preferred, in particular pharmaceutically acceptable salts, for example alkali metal or alkaline earth metal salts or hydrochlorides, sulfates, hemisulfates, methylsulfonates, p-toluenesulfonates, phosphates, and salts of amino acids, natural bases or carboxylic acids such as lactates, citrates, tartrates, acetates, adipates, fumarates, gluconates, glutamates, maleates or palmoates. Physiologically acceptable salts are prepared from compounds of the formula I capable of salt formation, including their stereoisomeric forms, in process step f) in a manner known per se. If compounds of the formula I or Ia contain acidic functionality, stable alkali metal, alkaline earth metal or optionally substituted ammonium salts can be formed with basic reagents such as hydroxides, carbonates, bicarbonates, alcoholates, and ammonia or organic bases, for example trimethyl- or triethylamine, ethanolamine, diethanolamine or triethanolamine, trometamol or else basic amino acids, for instance lysine, ornithine or arginine. Basic groups of the compounds of the formula I form acid addition salts with acids. Suitable for this purpose are both inorganic and organic acids such as hydrochloric or hydrobromic, sulfuric, hemisulfuric, phosphoric, methanesulfonic, benzenesulfonic, p-toluenesulfonic, 4-bromobenzenesulfonic, cyclohexylamidosulfonic, trifluoromethylsulfonic, 2-hydroxyethanesulfonic, acetic, oxalic, tartaric, succinic, glycerolphosphoric, lactic, malic, adipic, citric, fumaric, maleic, gluconic, glucuronic, palmitic or trifluoroacetic acid.

The compounds of the formulae I and Ia may contain one or more asymmetric carbon atoms and occur in the form of diastereomers or enantiomers or mixtures thereof. If a compound of the formula I or Ia occurs as a mixture of diastereomers or enantiomers or results as mixtures thereof in the chosen synthesis, it can be separated into the pure stereoisomers either by chromatography on an optionally chiral support material or, if the racemic compound of the formula I or Ia is capable of salt formation, it is also possible to carry out a fractional crystallization of the diastereomeric salts formed with an optically active base or acid as auxiliary. Examples of suitable chiral stationary phases for thin-layer or column chromatographic separation of enantiomers are modified silica gel supports (called Pirkle phases) and high molecular weight carbohydrates such as triacetylcellulose. For analytical purposes it is also possible to use gas chromatographic methods on chiral stationary phases after appropriate derivatization known to the skilled worker. To separate enantiomers of the racemic carboxylic acids, the diastereomeric salts of differing solubility are formed with an optically active, usually commercially available, base such as (−)-nicotine, (+)- and (−)-phenylethylamine, quinine bases, L-lysine or L- and D-arginine, the less soluble component is isolated as solid, the more soluble diastereomer is deposited from the mother liquor, and the pure enantiomers are obtained from the diastereomeric salts obtained in this way. It is possible in the same way in principle to convert the racemic compounds of the formula I or Ia which contain a basic group such as an amino group, with optically active acids such as (+)-camphor-10-sulfonic acid, D- and L-tartaric acid, D- and L-lactic acid, and (+) and (−)-mandelic acid, into the pure enantiomers. It is also possible to convert chiral compounds containing alcohol or amine functions with appropriately activated or, where appropriate, N-protected enantiomerically pure amino acids into the corresponding esters or amides, or conversely chiral carboxylic acids with carboxy-protected enantiomerically pure amino acids into the amides or with enantiomerically pure hydroxy carboxylic acids such as lactic acid into the corresponding chiral esters. The chirality of the amino acid or alcohol residue which has been introduced in enantiomerically pure form can then be utilized to separate the isomers by carrying out a separation of the diastereomers which are now available by crystallization or chromatography on suitable stationary phases, and then eliminating the included chiral moiety again by suitable methods.

A further possibility with some of the compounds of the formula I or Ia is to prepare the framework structures from diastereomerically or enantiomerically pure starting materials. It is thus possible also to employ other or simplified processes for purifying the final products. These starting materials have previously been prepared enantiomerically or diastereomerically pure by processes known from the literature.

This may mean in particular that either enantioselective processes are employed in the synthesis of the basic structures, or else a separation of enantiomers or diastereomers is carried out at an early stage of the synthesis and not at the stage of the final products. A simplification of the separations can likewise be achieved by proceeding in two or more stages.

The invention also relates to medicaments and pharmaceutical preparations having an effective content of at least one compound of the formula I or Ia and/or a physiologically tolerated salt of the compound of the formula I or Ia and/or a stereoisomeric or tautomeric form of the compound of the formula I or Ia, together with a pharmaceutically suitable and physiologically acceptable carrier, additive and/or other active compounds and auxiliaries. The invention furthermore relates to a compound of the formula I or Ia and/or all stereoisomeric or tautomeric forms of the compound of the formula I or Ia and/or mixtures of these forms in any ratio, and/or a physiologically acceptable salt of the compound of the formula I or Ia, for use as a pharmaceutic or active compound in a medicament.

By virtue of the pharmacological properties, the compounds of the invention are suitable for example for the prophylaxis, secondary prevention and therapy of all disorders which can be treated by inhibition of the protease-activated receptor 1 (PAR1). Thus, the compounds of the invention are suitable both for a prophylactic and a therapeutic use on humans. They are suitable both for acute treatment and for chronic treatment with long-term therapy. The compounds of the formulae I and Ia can be employed in patients suffering from impairments of well being or diseases associated with thromboses, embolisms, hypercoaguability or fibrotic changes. These include myocardial infarction, angina pectoris and all other types of acute coronary syndrome, acute stroke or its secondary prevention, peripheral vascular disorders, deep vein thrombosis, pulmonary embolism, embolic or thrombotic events caused by cardiac arrhythmias, cardiovascular events such as restenosis following revascularization, angioplasty and similar procedures such as stent implantations and bypass operations.

The compounds of the formulae I and Ia can further be employed in all procedures leading to contact of blood with foreign surfaces, such as for dialysis patients and patients with indwelling catheters. Compounds of the formulae I and Ia can be employed in order to reduce the risk of thrombosis following surgical procedures such as knee and hip joint operations. Compounds of the formulae I and Ia are suitable for the treatment of patients with disseminated intravascular coagulation, sepsis and other intravascular events associated with inflammation.

The compounds of the formulae I and Ia are further suitable for the prophylaxis and treatment of patients with atherosclerosis, diabetes and the metabolic syndrome and the sequelae thereof. Impairments of the hemostatic system (for example fibrin deposits) have been implicated in mechanisms leading to tumor growth and tumor metastasis, and in inflammatory and degenerative articular disorders such as rheumatoid arthritis and arthrosis. Compounds of the formulae I and Ia are suitable for retarding or preventing such processes.

Further indications for the use of the compounds of the formulae I and Ia are fibrotic changes in the lung such as chronic obstructive pulmonary disease, adult respiratory distress syndrome (ARDS) and of the eye such as fibrin deposits following eye operations. Compounds of the formulae I and Ia are also suitable for the prevention and/or treatment of scarring.

The medicaments of the invention can be administered by oral, inhalational, rectal or transdermal administration or by subcutaneous, intraarticular, intraperitoneal or intravenous injection. Oral administration is preferred. Coating of stents with compounds of the formula I or Ia and other surfaces which come into contact with blood in the body is also possible.

The invention also relates to a process for manufacturing a medicament, which comprises making a suitable dosage form from at least one compound of the formula I or Ia with a pharmaceutically suitable and physiologically acceptable carrier and, where appropriate, further suitable active compounds, additives or auxiliaries.

Suitable solid or pharmaceutical formulations are, for example, granules, powder, coated tablets, tablets, (micro) capsules, suppositories, syrups, solutions, suspensions, emulsions, drops or injectable solutions, and products with protracted release of active compound, in the production of which customary aids such as carriers, disintegrants, binders, coating agents, swelling agents, glidants or lubricants, flavorings, sweeteners and solubilizers are used. Auxiliaries which are frequently used and which may be mentioned are magnesium carbonate, titanium dioxide, lactose, mannitol and other sugars, talc, milk protein, gelatin, starch, cellulose and its derivatives, animal and vegetable oils such as fish liver oil, sunflower, peanut or sesame oil, polyethylene glycol and solvents such as, for example, sterile water and monohydric or polyhydric alcohols such as glycerol.

The pharmaceutical products are preferably manufactured and administered in dosage units, where each unit comprises as active constituent a particular dose of the compound of the invention of the formula I or Ia. In the case of solid dosage units such as tablets, capsules, coated tablets or suppositories, this dose can be up to about 1000 mg, but preferably about 50 to 300 mg and, in the case of injection solutions in ampoule form, up to about 300 mg but preferably about 10 to 100 mg.

The daily doses indicated for the treatment of an adult patient weighing about 70 kg are, depending on the activity of the compound of the formula I or Ia, from about 2 mg to 1000 mg of active compound, preferably about 50 mg to 500 mg. However, in some circumstances, higher or lower daily doses may also be appropriate. The daily dose can be administered either by a single administration in the form of a single dosage unit or else a plurality of smaller dosage units or by multiple administration of divided doses at particular intervals.

Compounds of the formula I or Ia can be administered both as monotherapy and in combination or together with all antithrombotics (anticoagulants and platelet aggregation inhibitors), thrombolytics (plasminogen activators of every type), other substances having profibrinolytic activity, antihypertensives, regulators of blood glucose, lipid-lowering agents and antiarrhythmics. Suitable platelet aggregation inhibitors in this connection are cyclooxygenase 1 inhibitors such as aspirin, irreversible $P2Y_{12}$ antagonists such as clopidogrel or prasugrel, reversible $P2Y_{12}$ antagonists such as cangrelor or AZD6140 and thromboxane $A_2$/prostaglandin $H_2$ antagonists such as terutroban. It has been possible to show additive effects of PAR1 blockade in combination with $P2Y_{12}$ blockade for example (M. Chintala et al., Eur. Heart J. 28 (Abstract Supplement 1): 188, 2007).

EXAMPLES

The prepared compounds were usually characterized by spectroscopic and chromatographic data, specifically mass spectra (MS) and HPLC retention times (Rt; in min), which were obtained by combined analytical HPLC/MS characterization (LC/MS). In the MS characterization, usually the mass number (m/z) of the peak of the molecular ion (M or $M^+$) or of a related ion such as the ion M+1 (or $M+1^+$; protonated molecular ion $M+H^+$), which formed depending on the ionization method used, is indicated. The ionization method generally used was electrospray ionization (ESI). The following LC/MS methods were used:

Method B
column: Chirapak IA/103 250×4.6 mm
solvent: Hep:EtOH:MeOH, isocratic 10:1:1
ionization: $ESI^+$
Method C
column: Chirapak IA/103 250×4.6 mm solvent: Hep:EtOH:MeOH, preconditioned with diethylamine, isocratic 10:1:1
ionization: ESI+
Method D
column: YMC J'sphere ODS H80 20×2.1 mm 4 μm
solvent: MeCN:H$_2$O+0.05% TFA (flow rate 1 ml/min)
gradient: from 4:96 (0 min) to 95:5 (2 min) to 95:5 (2.4 min) to 96:4 (2.45 min)
ionization: ESI+
Method E
column: Chirapak IA/104 250×4.6 mm
solvent: MeCN+0.1% diethylamine. isocratic
ionization: ESI+
Method J
column: Luna C18 10×2 mm 3 μm
solvent: MeCN+0.05% TFA:H$_2$O+0.05% TFA (flow rate 1.1 ml/min)
gradient: 7:93 (0 min) to 95:5 (1.2 min) to 95:5 (1.4 min) to 7:93 (1.45 min)
ionization: ESI+

The compounds were further characterized by $^1$H NMR spectroscopy. The abbreviations used are either explained or correspond to usual conventions. Evaporation of solvents usually took place under reduced pressure at 35° C. to 45° C. in a rotary evaporator and is described as "freed of solvent", "concentrated", "evaporated" or "solvent removed". The reactions took place in standard reaction apparatuses such as one-neck or multineck flasks which, unless otherwise described, had volumes of from 5 ml to 2000 ml appropriate for requirements and were equipped with septum, stoppers, condenser, stirrer or other items of equipment as required. Unless mentioned otherwise, all the reactions took place under argon as protective gas and were stirred with magnetic stirrers.

Abbreviations Used:
DCM dichloromethane
DME 1,2-dimethoxyethane
DMF dimethylformamide
DMSO dimethyl sulfoxide
EDCI N-(3-dimethylaminopropyl)-N'-ethylcarbodiimide hydrochloride
EtOH ethanol
HATU O-(7-azabenzotriazol-1-yl)-N,N,N',N'-tetramethyluronium hexafluorophosphate
Hep heptane
HOBt 1-hydroxy-1H-benzotriazole hydrate
MeCN acetonitrile
MeOH methanol
NMM N-methylmorpholine
RT room temperature (20° C. to 25° C.)
Rt retention time
sat. saturated
TFA trifluoroacetic acid A plurality of diastereomers is usually formed in the reactions and can be separated as racemic mixtures by column chromatography. Unless indicated, the assignment of these racemic mixtures to particular configurations is not yet unambiguous. Likewise, the absolute assignment of the pure diastereomers obtained from the racemic mixtures by chiral column chromatography has not been done. Where a defined stereochemistry is indicated, the assignment was derived from the coupling constants of the hydrogen atoms in the pyrrole ring by NMR spectroscopy methods.

Example 1

5-(3-Fluorophenyl)pyridine-2-carbaldehyde

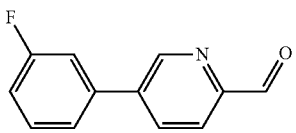

A mixture of 2 g of 5-bromopyridine-2-carbaldehyde, 1.96 g of 3-fluorophenylboronic acid, 11.2 g of K$_2$CO$_3$, 160 ml of toluene, 60 ml of water, 60 ml of ethanol and 0.93 mg of tetrakis(triphenylphosphine)palladium (0) is stirred at 100° C. under argon for 2 hours. The solvents are evaporated and the residue is dispersed in 100 ml of water, and the product is extracted with 2 portions of 30 ml of ethyl acetate. The organic phase is washed with 30 ml of sat. brine, dried over sodium sulfate and concentrated. The resulting residue is recrystallized from 28 ml of isopropanol.
Yield: 1.3 g, LC/MS (method D): m/z=202 (M+1); Rt=1.317 min Example 2

(E)-3-[5-(3-Fluorophenyl)pyridin-2-yl]propenal

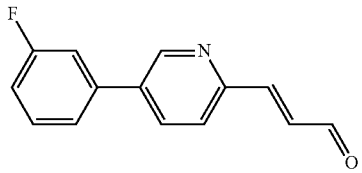 [SMILES: O=C/C=C/c1ccc(-c2cccc(F)c2)cn1]

584 mg of 5-(3-fluorophenyl)pyridine-2-carbaldehyde and 883 mg of (triphenylphosphoranylidene)acetaldehyde are stirred at RT overnight. The solvent is evaporated and the residue is purified by column chromatography (silica gel, MeOH:DCM=99.5:0.5).
Yield: 450 mg, LC/MS (method J): m/z=228 (M+1); Rt=0.887 min Example 3

(E)-3-(5-Bromopyridin-2-yl)propenal

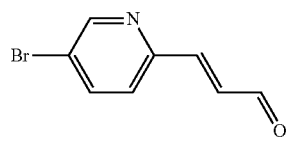 [SMILES: O=C/C=C/c1ccc(Br)cn1]

818 mg of (triphenylphosphoranylidene)acetaldehyde and 500 mg of 5-bromopyridinecarbaldehyde are stirred at RT overnight. The volatile fractions are removed under reduced pressure, and the residue is purified by column chromatography (silica gel, MeOH:DCM=99:1).

Yield: 415 mg; LC/MS (method D): m/z=213 (M+1); Rt=1.121 min

Example 4

5-Nitro-1H-pyrazole-3-cyclopropylmethylcarboxamide

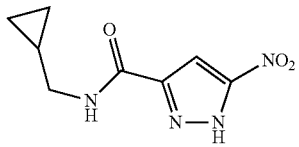 [SMILES: Nc1cc(C(=O)NCC2CC2)n[nH]1]

7.5 g of 5-nitro-1H-pyrazole-3-carboxylic acid were dissolved in 70 ml of DMF. 19.9 g of HATU and 9.6 g of triethylamine are added at RT and, after stirring for 10 minutes, 5.1 g of aminomethylcyclopropane hydrochloride are added, and the mixture is stirred at RT overnight. After aqueous workup, the crude product is purified by column chromatography (silica gel, methanol:DCM=1:30).

Yield: 5 g; LC/MS (method J): m/z=211 (M+1); Rt=0.617 min

Example 5

5-Amino-1H-pyrazole-3-cyclopropylmethylcarboxamide

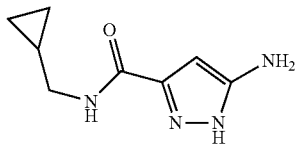

1 g of 5-nitro-1H-pyrazole-3-cyclopropylmethylcarboxamide is dissolved in 30 ml of methanol and 2 ml of acetic acid. This mixture is hydrogenated in the presence of 110 mg of Pd/C under 5 bar until reaction is complete. The mixture is filtered through celite, evaporated to dryness and purified by column chromatography (silica gel, methanol:DCM=1:30).

Yield: 805 mg; LC/MS (method J): m/z=181 (M+1); Rt=0.170 min

All 5-amino-1H-pyrazole-3-carboxamides were prepared in this manner, unless stated otherwise.

General Procedure for Three-Component Coupling in Ethanol (Method A)

Equimolar amounts of the corresponding amino-1H-pyrazole-3-carboxamide unit, of the cyclic diketone and (E)-3-[5-(3-fluorophenyl)pyridin-2-yl]propenal were dissolved in EtOH and heated at reflux for 2 to 12 h. After cooling, the mixture was concentrated and purified by column chromatography on silica gel.

General Procedure for Three-Component Coupling in a 1,4-Dioxane/Water Mixture (Method B)

Equimolar amounts of the corresponding amino-1H-pyrazole-3-carboxamide unit, of the cyclic diketone and (E)-3-[5-(3-fluorophenyl)pyridin-2-yl]propenal were dissolved in a mixture of 1,4-dioxane/water (2:1) and heated to 30° C. to 80° C. for 1 to 12 h. After cooling, the mixture was concentrated and purified by column chromatography on silica gel.

General Procedure for Suzuki Coupling (Method C)

The corresponding aryl bromide (1 eq), the corresponding boronic acid (1.5 eq), $K_3PO_4$ (2.5 eq) and 1,1'-bis(diphenylphosphino)ferrocenepalladium dichloride (20 mol %) were dissolved in a mixture of DME/n-butanol/water (2:2:1). Argon was bubbled through the solution for 10 min. Thereafter, the mixture was heated to 120° C. to 150° C. in a microwave for 1 to 4 hours. After cooling, the mixture was concentrated, and the remaining residue was taken up in DCM and washed with sat. $NaHCO_3$ solution. The organic phase was dried over $Na_2SO_4$, concentrated and purified by column chromatography on silica gel.

Example 6

4-{(E)-2-[5-(3-Fluorophenyl)pyridin-2-yl]vinyl}-7,7-dimethyl-5-oxo-4,5,6,7,8,9-hexahydro-1H-pyrazolo[3,4-b]quinoline-3-cyclopropylmethylcarboxamide

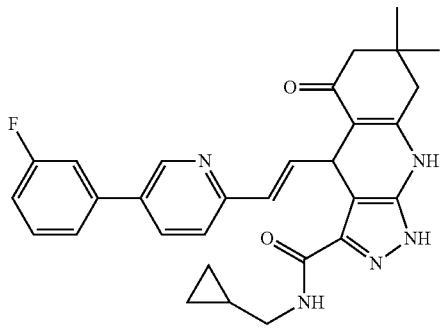 [SMILES: CC1(C)CC(=O)C2=C(C1)Nc1[nH]nc(C(=O)NCC3CC3)c1C2/C=C/c1ccc(-c2cccc(F)c2)cn1]

According to general procedure A, a mixture of 50 mg of (E)-3-[5-(3-fluorophenyl)pyridin-2-yl]propenal, 40 mg of 5-amino-1H-pyrazole-3-cyclopropylmethylcarboxamide, 31 mg of dimedone and 5 ml of ethanol is boiled under reflux for 2 hours. After cooling, the mixture is concentrated and purified by column chromatography (silica gel, methanol:DCM=5:95).

Yield: 25 mg; LC/MS (method J): m/z=512 (M+1); Rt=0.786 min

Example 7

7,7-Dimethyl-4-[(E)-2-(6-methylpyridin-2-yl)vinyl]-5-oxo-4,5,6,7,8,9-hexahydro-1H-pyrazolo[3,4-b]quinoline-3-isopropylcarboxamide

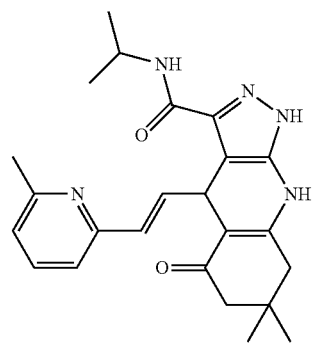 [SMILES: Cc1cccc(/C=C/C2C3=C(CC(C)(C)CC3=O)Nc3[nH]nc(C(=O)NC(C)C)c32)n1]

The title compound is prepared analogously to procedure A from 100 mg of (E)-3-(6-methylpyridin-2-yl)propenal, 95 mg of dimedone and 114 mg of 5-amino-1H-pyrazole-3-isopropylcarboxamide.

Yield: 7 mg; LC/MS (method D): m/z=420 (M+1); Rt=0.877 min

Example 8

4-{(E)-2-[5-(3-Fluorophenyl)pyridin-2-yl]vinyl}-7,7-dimethyl-5-oxo-4,5,6,7,8,9-hexahydro-1H-pyrazolo[3,4-b]quinoline-3-isopropylcarboxamide

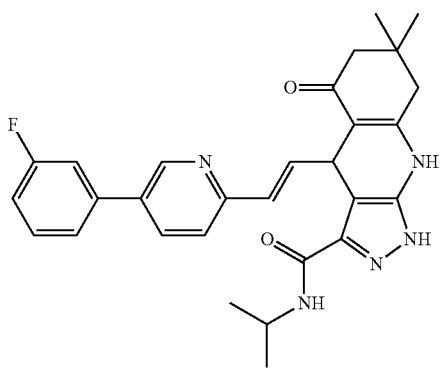 [SMILES: CC(C)NC(=O)c1n[nH]c2c1C(/C=C/c1ccc(-c3cccc(F)c3)cn1)C1=C(CC(C)(C)CC1=O)N2]

The title compound is prepared according to procedure A from 50 mg of (E)-3-[5-(3-fluorophenyl)pyridin-2-yl]propenal, 31 mg of dimedone and 37 mg of 5-amino-1H-pyrazole-3-isopropylcarboxamide.

Yield: 35 mg; LC/MS (method J): m/z=500 (M+1); Rt=0.766 min

Example 9

4-{(E)-2-[5-(3-Fluorophenyl)pyridin-2-yl]vinyl}-6,6-dimethyl-5-oxo-4,5,6,7,8,9-hexahydro-1H-pyrazolo[3,4-b]quinoline-3-cyclopropylmethylcarboxamide

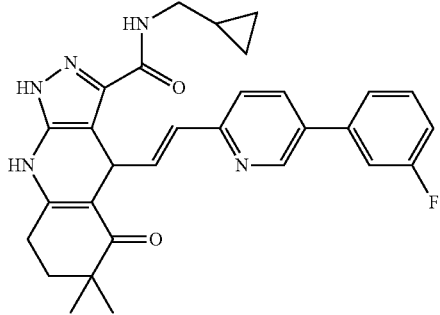 [SMILES: CC1(C)CCC2=C(C1=O)C(/C=C/c1ccc(-c3cccc(F)c3)cn1)c1c(C(=O)NCC3CC3)n[nH]c1N2]

The title compound is prepared according to procedure A from 50 mg of (E)-3-[5-(3-fluorophenyl)pyridin-2-yl]propenal, 31 mg of 4,4-dimethylcyclohexane-1,3-dione and 40 mg of 5-amino-1H-pyrazole-3-cyclopropylmethylcarboxamide.

Yield: 35 mg; LC/MS (method J): m/z=512 (M+1); Rt=0.784 min

Example 10

4-{(E)-2-[5-(3-Fluorophenyl)pyridin-2-yl]vinyl}-7-isopropyl-5-oxo-4,5,6,7,8,9-hexahydro-1H-pyrazolo[3,4-b]quinoline-3-cyclopropylmethylcarboxamide

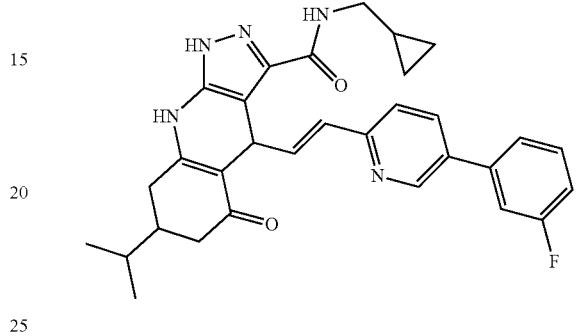

The title compound is prepared as a mixture of diastereomers according to procedure A from 50 mg of (E)-3-[5-(3-fluorophenyl)pyridin-2-yl]propenal, 34 mg of 5-isopropylcyclohexane-1,3-dione and 40 mg of 5-amino-1H-pyrazole-3-cyclo-propylmethylcarboxamide.

Yield: 30 mg; LC/MS (method J): m/z=526 (M+1); Rt=0.823 min

Example 11

4-{(E)-2-[5-(3-Fluorophenyl)pyridin-2-yl]vinyl}-7-methyl-5-oxo-4,5,6,7,8,9-hexahydro-1H-pyrazolo[3,4-b]quinoline-3-isopropylcarboxamide

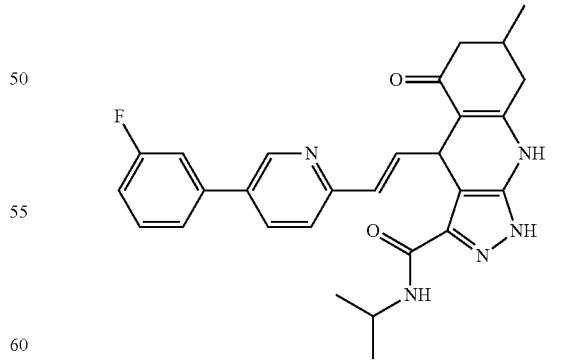

The title compound is prepared as mixture of diastereomers according to procedure A from 50 mg of (E)-3-[5-(3-fluorophenyl)pyridin-2-yl]propenal, 27 mg of 5-methylcyclohexane-1,3-dione and 37 mg of 5-amino-1H-pyrazole-3-isopropyl-carboxamide.

Yield: 35 mg; LC/MS (method J): m/z=486 (M+1); Rt=0.722 min

Example 12

4-{(E)-2-[5-(3-Fluorophenyl)pyridin-2-yl]vinyl}-7-methyl-5-oxo-4,5,6,7,8,9-hexahydro-1H-pyrazolo[3,4-b]quinoline-3-cyclopropylmethylcarboxamide

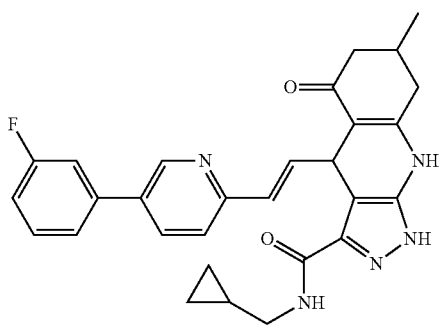 [SMILES: CC1CC(=O)C2=C(C1)Nc1[nH]nc(C(=O)NCC3CC3)c1C2/C=C/c1ccc(-c2cccc(F)c2)cn1]

The title compound is prepared as a mixture of diastereomers according to procedure A from 200 mg of (E)-3-[5-(3-fluorophenyl)pyridin-2-yl]propenal, 111 mg of 5-methylcyclohexane-1,3-dione and 159 mg of 5-amino-1H-pyrazole-3-cyclopropyl methylcarboxamide.

Yield: 183 mg; LC/MS (method J): m/z=498 (M+1); Rt=0.758 min

Example 13

Separation of the Mixture of Diastereomers from Example 12

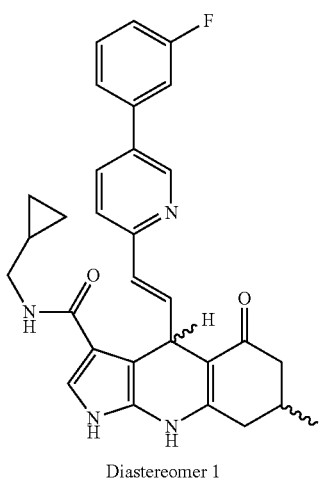
Diastereomer 1

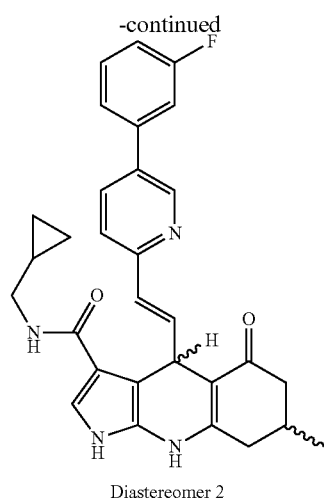
Diastereomer 2

The mixture of diastereomers from example 12 is separated by chiral chromatography (HPLC column: Chiralcel OD-H/61, 250×4.6 mm, mobile phase: heptane:ethanol:MeOH 10:1:1, flow rate: 1 ml/min, 30° C.) and afforded 2 pure diastereomers as main products of as yet undetermined absolute configuration.

Yields:
(Diastereomer 1): 54 mg; m/z=498 (M+1); Rt=8.349 min
(Diastereomer 2): 58 mg; m/z=498 (M+1); Rt=9.400 min Example 14

Ethyl 4-{(E)-2-[5-(3-fluorophenyl)pyridin-2-yl]vinyl}-7,7-dimethyl-5-oxo-4,5,6,7,8,9-hexahydro-1H-pyrazolo[3,4-b]quinoline-3-carboxylate

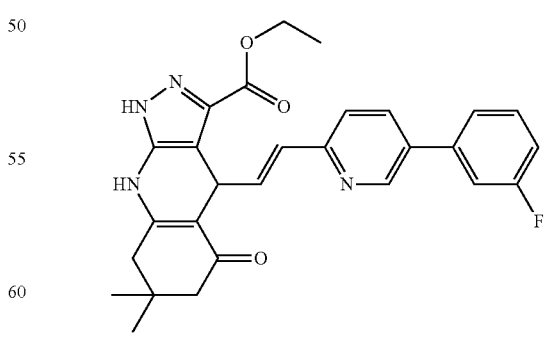

The title compound is prepared as a mixture of diastereomers according to procedure A from 150 mg of (E)-3-[5-(3-fluorophenyl)pyridin-2-yl]propenal, 93 mg of dimedone and 102 mg of ethyl 5-amino-1H-pyrazole-3-carboxylate.

Yield: 72 mg; LC/MS (method D): m/z=487 (M+1); Rt=1.115 min

Example 15

4-{(E)-2-[5-(3-Fluorophenyl)pyridin-2-yl]vinyl}-7,7-dimethyl-5-oxo-4,5,6,7,8,9-hexahydro-1H-pyrazolo[3,4-b]quinoline-3-(2,2-dimethylpropyl)carboxamide

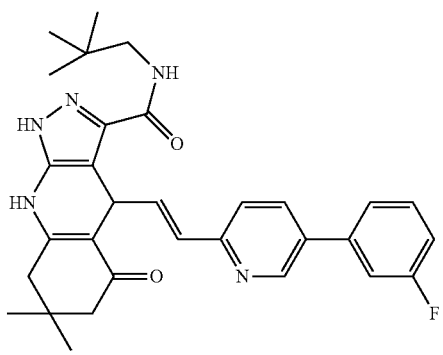 [SMILES: CC(C)(C)CNC(=O)c1n[nH]c2c1C(/C=C/c1ccc(-c3cccc(F)c3)cn1)C1=C(CC(C)(C)CC1=O)N2]

The title compound is prepared according to procedure A from 174 mg of (E)-3-[5-(3-fluorophenyl)pyridin-2-yl]propenal, 107 mg of dimedone and 150 mg of 5-amino-1H-pyrazole-3-(2,2-dimethylpropyl)carboxamide.

Yield: 102 mg; LC/MS (method J): m/z=528 (M+1); Rt=0.811 min

Example 16

4'-{(E)-2-[5-(3-Fluorophenyl)pyridin-2-yl]vinyl}-5-oxo-4',5',6',7',8',9'-hexahydro-spiro{cyclopentane-1,7-1H-pyrazolo[3,4-b]quinoline}-3'-cyclopropylmethyl-carboxamide

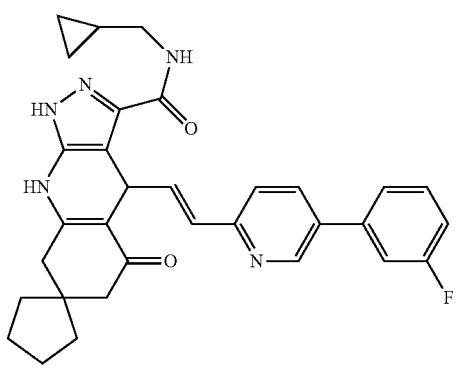 [SMILES: O=C1CC2(CCCC2)CC2=C1C(/C=C/c1ccc(-c3cccc(F)c3)cn1)c1c(C(=O)NCC3CC3)n[nH]c1N2]

The title compound is prepared according to procedure A from 151 mg of (E)-3-[5-(3-fluorophenyl)pyridin-2-yl]propenal, 111 mg of spiro[4.5]decane-7,9-dione and 120 mg of 5-amino-1H-pyrazole-3-cyclopropylmethylcarboxamide.

Yield: 52 mg; LC/MS (method J): m/z=538 (M+1); Rt=0.808 min

Example 17

4-{(E)-2-[5-(3-Fluorophenyl)pyridin-2-yl]vinyl}-7,7-dimethyl-5-oxo-4,5,6,7,8,9-hexahydro-1H-pyrazolo[3,4-b]quinoline-3-(1-ethylcyclobutylmethyl) carboxamide

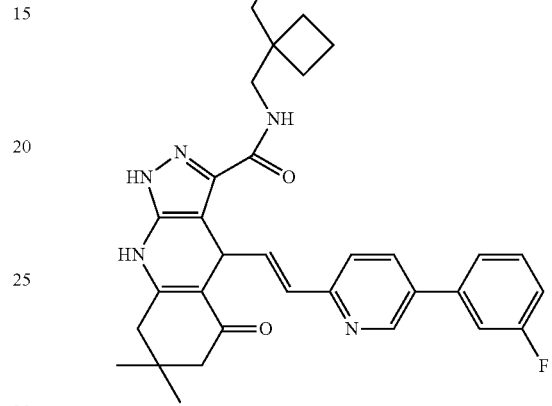

The title compound is prepared according to procedure B from 123 mg of (E)-3-[5-(3-fluorophenyl)pyridin-2-yl]propenal, 76 mg of dimedone and 120 mg of 5-amino-1H-pyrazole-3-(1-ethylcyclobutylmethyl)carboxamide.

Yield: 71 mg; LC/MS (method J): m/z=554 (M+1); Rt=0.855 min

Example 18 tert-Butyl 5-amino-1H-pyrazole-3-carboxylate

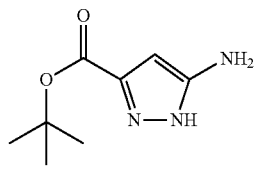

2 g of 5-nitro-3-pyrazolecarboxylic acid are dissolved in THF (5 ml), then diluted with toluene (40 ml) and heated at reflux. 10.35 g of N,N-dimethylformamide-di-tert-butyl acetal are added dropwise and the mixture is heated under reflux for 8 h. After cooling to RT, the solvent is removed under reduced pressure and the residue is taken up in DCM. It is washed with water and twice with sat. NaHCO$_3$ solution. The organic phase is dried over Na$_2$SO$_4$ and concentrated. The residue is purified by column chromatography (silica gel, MeOH:DCM=1-10:99-90). The 1.26 g of tert-butyl 5-nitro-1H-pyrazole-3-carboxylate thus obtained are dissolved in MeOH (10 ml) and admixed with 88 mg of palladium on carbon (10%). Hydrogenation is effected at hydrogen pressure 4.5 bar for 2 h. The solution is filtered and the solvent is removed under reduced pressure. Yield: 1.08 g; LC/MS (method J): m/z=128 (M–tBu); Rt=0.477 min

Example 19 tert-Butyl 4-{(E)-2-[5-(3-fluorophenyl)pyridin-2-yl]vinyl}-7,7-dimethyl-5-oxo-4,5,6,7,8,9-hexahydro-1H-pyrazolo[3,4-b]quinoline-3-carboxylate

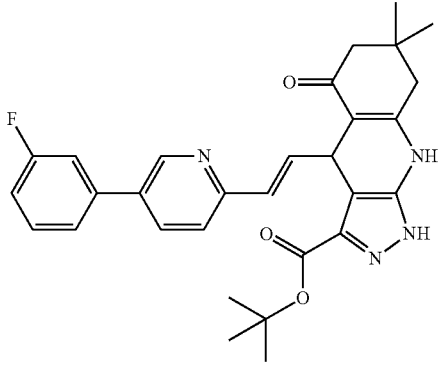 [SMILES: CC1(C)CC(=O)C2=C(C1)Nc1[nH]nc(C(=O)OC(C)(C)C)c1C2/C=C/c1ccc(-c2cccc(F)c2)cn1]

The title compound is prepared according to procedure A from 620 mg of (E)-3-[5-(3-fluorophenyl)pyridin-2-yl]propenal, 383 mg of dimedone and 500 mg of tert-butyl 5-amino-1H-pyrazole-3-carboxylate.

Yield: 149 mg; LC/MS (method J): m/z=515 (M+1); Rt=0.854 min

Example 20

4-{(E)-2-[5-(3-Fluorophenyl)pyridin-2-yl]vinyl}-7,7-dimethyl-5-oxo-4,5,6,7,8,9-hexahydro-1H-pyrazolo[3,4-b]quinoline-3-carboxylic acid

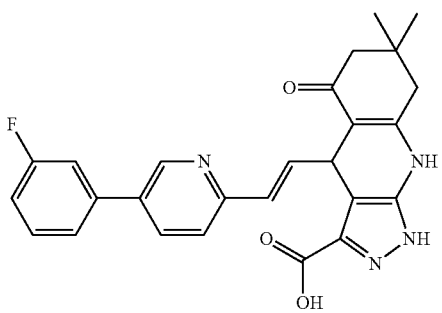 [SMILES: CC1(C)CC(=O)C2=C(C1)Nc1[nH]nc(C(=O)O)c1C2/C=C/c1ccc(-c2cccc(F)c2)cn1]

83 mg of tert-butyl 4-{(E)-2-[5-(3-fluorophenyl)pyridin-2-yl]vinyl}-7,7-dimethyl-5-oxo-4,5,6,7,8,9-hexahydro-1H-pyrazolo[3,4-b]quinoline-3-carboxylate are dissolved in DCM (2.5 ml), admixed with TFA (2.5 ml) and stirred at RT for 3 h. The solvent is removed under reduced pressure, and the residue is suspended in toluene and concentrated by rotary evaporation once again. The resulting solid is used further without purification.

Yield: 120 mg; LC/MS (method J): m/z=459 (M+1); Rt=0.703 min

Example 21

4-{(E)-2-[5-(3-Fluorophenyl)pyridin-2-yl]vinyl}-7,7-dimethyl-5-oxo-4,5,6,7,8,9-hexahydro-1H-pyrazolo[3,4-b]quinoline-3-(1-aminomethylcyclobutylmethyl)carboxamide

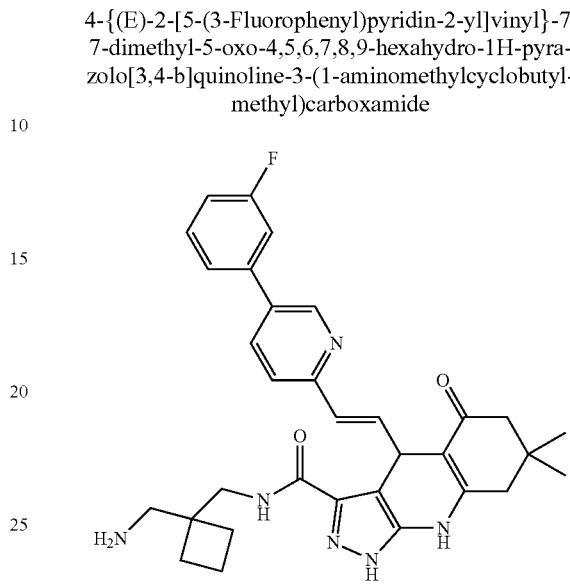

92 mg of 4-{(E)-2-[5-(3-fluorophenyl)pyridin-2-yl]vinyl}-7,7-dimethyl-5-oxo-4,5,6,7,8,9-hexahydro-1H-pyrazolo[3,4-b]quinoline-3-carboxylic acid, 35 mg of HOBt, 44 mg of EDCI, 202 mg of NMM and 75 mg of C-(1-aminomethylcyclobutyl)methylamine hydrochloride are suspended in DMF (0.5 ml). Then water (160 µl) is added and the solution which then formed is stirred at RT for 3 h. The reaction mixture is admixed with sat. NaHCO₃ solution and ethyl acetate. The organic phase is removed and the aqueous phase is extracted three times more with ethyl acetate. The combined organic phases are dried over Na₂SO₄ and concentrated. The residue is purified by chromatography (silica gel, MeOH:DCM)

Yield: 57 mg; LC/MS (method J): m/z=555 (M+1); Rt=0.682 min

Example 22 tert-Butyl {3-[(5-amino-1H-pyrazole-3-carbonyl)amino]-2,2-dimethylpropyl}carbamate

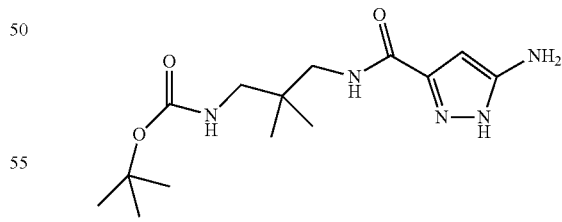

2.00 g of 5-nitro-3-pyrazolecarboxylic acid, 2.24 g of HOBt, 2.81 g of EDCI, 3.86 g of NMM and 2.58 g of 1-Boc-amino-2,2-dimethyl-1,3-propanediamine are dissolved in DMF (30 ml) and the solution is stirred at RT for 8 h. The reaction mixture is admixed with sat. NaHCO₃ solution and ethyl acetate. The organic phase is removed and the aqueous phase is extracted three times more with ethyl acetate. The combined organic phases are dried over Na₂SO₄ and concentrated. The residue is purified by chromatography (silica gel, ethyl acetate:heptane). The 3.21 g of tert-butyl {3-[(5-nitro- 1H-pyrazole-3-carbonyl)amino]-2,2-dimethylpropyl}carbamate thus obtained are dissolved in MeOH (20 ml) and admixed with 140 mg of palladium on carbon (10%). Hydrogenation is effected with hydrogen pressure 4.5 bar for 3 h. The solution is filtered and the solvent is removed under reduced pressure.

Yield: 2.95 g; LC/MS (method J): m/z=312 (M–tBu); Rt=0.651 min

Example 23

3-tert-Butoxycarbonylamino-2,2-dimethylpropyl 4-{(E)-2-[5-(3-fluorophenyl)pyridin-2-yl]vinyl}-7,7-dimethyl-5-oxo-4,5,6,7,8,9-hexahydro-1H-pyrazolo[3,4-b]quinoline-3-carboxylate

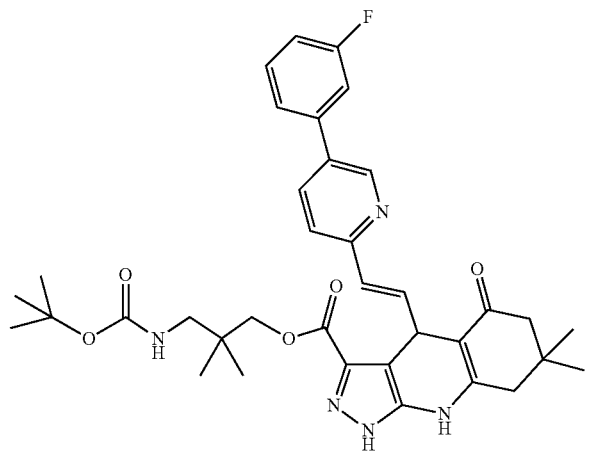 [SMILES: CC(C)(CNC(=O)OC(C)(C)C)COC(=O)c1n[nH]c2c1C(/C=C/c1ccc(-c3cccc(F)c3)cn1)C1=C(CC(C)(C)CC1=O)N2]

The title compound is prepared according to procedure A from 110 mg of (E)-3-[5-(3-fluorophenyl)pyridin-2-yl]propenal, 68 mg of dimedone and 150 mg of tert-butyl {3-[(5-amino-1H-pyrazole-3-carbonyl)amino]-2,2-dimethylpropyl}carbamate.

Yield: 113 mg; LC/MS (method J): m/z=643 (M+1); Rt=0.885 min

Example 24

3-Amino-2,2-dimethylpropyl 4-{(E)-2-[5-(3-fluorophenyl)pyridin-2-yl]-vinyl}-7,7-dimethyl-5-oxo-4,5,6,7,8,9-hexahydro-1H-pyrazolo[3,4-b]quinoline-3-carboxylate trifluoroacetic acid salt

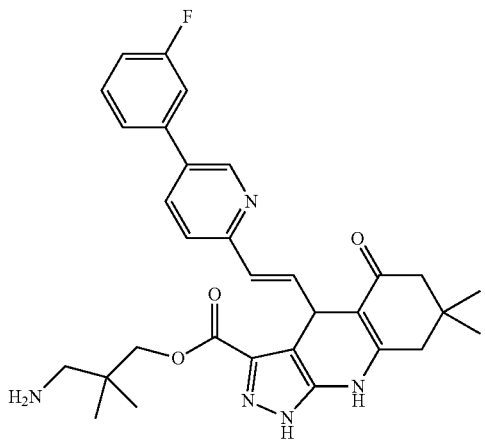 [SMILES: CC(C)(CN)COC(=O)c1n[nH]c2c1C(/C=C/c1ccc(-c3cccc(F)c3)cn1)C1=C(CC(C)(C)CC1=O)N2]

40 mg of 3-tert-butoxycarbonylamino-2,2-dimethylpropyl 4-{(E)-2-[5-(3-fluorophenyl)pyridin-2-yl]vinyl}-7,7-dimethyl-5-oxo-4,5,6,7,8,9-hexahydro-1H-pyrazolo[3,4-b]quinoline-3-carboxylate are dissolved in DCM (2.5 ml), admixed with TFA (2.5 ml) and stirred at RT for 3 h. The solvent is removed under reduced pressure, and the residue is suspended in toluene and concentrated by rotary evaporation once again. Yield: 63 mg; LC/MS (method J): m/z=543 (M+1); Rt=0.680 min

Example 25

4-[(E)-2-(5-Bromopyridin-2-yl)vinyl]-7,7-dimethyl-5-oxo-4,5,6,7,8,9-hexahydro-1H-pyrazolo[3,4-b]quinoline-3-cyclopropylmethylcarboxamide

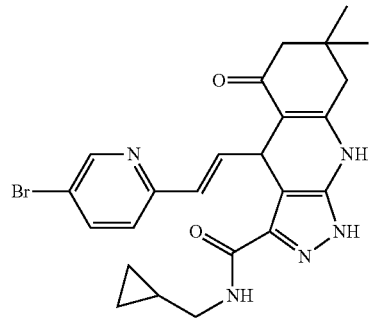 [SMILES: CC1(C)CC(=O)C2=C(C1)Nc1[nH]nc(C(=O)NCC3CC3)c1C2/C=C/c1ccc(Br)cn1]

The title compound is prepared analogously to procedure A from 150 mg of (E)-3-(5-bromopyridin-2-yl)propenal, 100 mg of dimedone and 127 mg of 5-amino-1H-pyrazole-3-cyclopropyl methylcarboxamide.

Yield: 133 mg; LC/MS (method J): m/z=497 (M+1); Rt=0.847 min

Example 26

4-[(E)-2-(5-Bromopyridin-2-yl)vinyl]-7,7-dimethyl-5-oxo-4,5,6,7,8,9-hexahydro-1H-pyrazolo[3,4-b]quinoline-3-isopropylcarboxamide

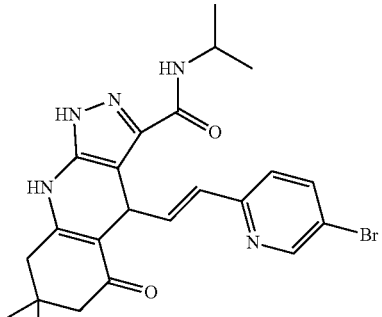

The title compound is prepared analogously to procedure A from 240 mg of (E)-3-(5-bromopyridin-2-yl)propenal, 159 mg of dimedone and 190 mg of 5-amino-1H-pyrazole-3-isopropylcarboxamide.

Yield: 135 mg; LC/MS (method D): m/z=485 (M+1); Rt=1.168 min

Example 27

4-[(E)-2-(5-Bromopyridin-2-yl)vinyl]-5'-oxo-4',5',6',7',8',9'-hexahydro-spiro{cyclopentane-1,7-1H-pyrazolo[3,4-b]quinoline}-3'-cyclopropylmethyl-carboxamide

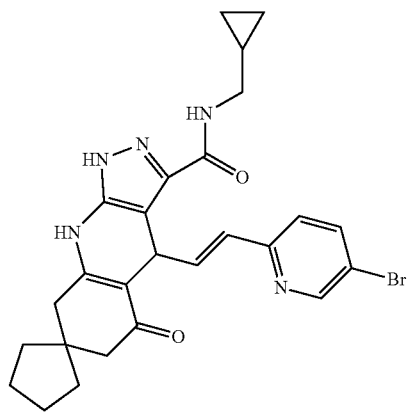 [SMILES: O=C1CC2(CCCC2)CC2=C1C(/C=C/c1ccc(Br)cn1)c1c(C(=O)NCC3CC3)n[nH]c1N2]

The title compound is prepared analogously to procedure A from 470 mg of (E)-3-(5-bromopyridin-2-yl)propenal, 434 mg of spiro[4.5]decane-7,9-dione and 553 mg of 5-amino-1H-pyrazole-3-cyclopropylmethylcarboxamide.

Yield: 825 mg; LC/MS (method J): m/z=523 (M+1); Rt=0.881 min

Example 28

4'-{(E)-2-[5-(3,5-Difluorophenyl)pyridin-2-yl]vinyl}-5'-oxo-4',5',6',7',8',9'-hexahydro-spiro{cyclopentane-1,7-1H-pyrazolo[3,4-b]quinoline}-3'-cyclopropylmethyl-carboxamide

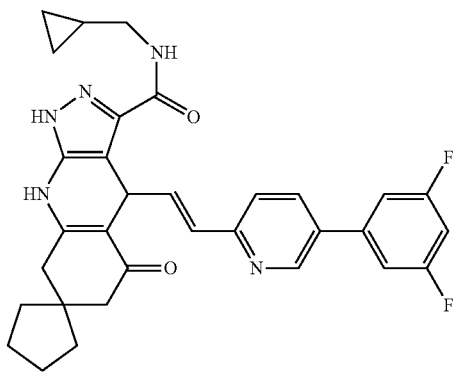 [SMILES: O=C1CC2(CCCC2)CC2=C1C(/C=C/c1ccc(-c3cc(F)cc(F)c3)cn1)c1c(C(=O)NCC3CC3)n[nH]c1N2]

The title compound is prepared according to procedure C from 150 mg of 4-[(E)-2-(5-bromopyridin-2-yl)vinyl]-5'-oxo-4',5',6',7',8',9'-hexahydrospiro{cyclopentane-1, 7-1H-pyrazolo[3,4-b]quinoline}-3'-cyclopropylmethylcarboxamide, 68 mg of 3,5-difluorophenylboronic acid, 153 mg of $K_3PO_4$ and 42 mg of 1,1'-bis(diphenyl-phosphino)ferrocenepalladium dichloride.

Yield: 47 mg; LC/MS (method J): m/z=556 (M+1); Rt=0.865 min

Example 29

4-{(E)-2-[5-(3,4-Difluorophenyl)pyridin-2-yl]vinyl}-7,7-dimethyl-5-oxo-4,5,6,7,8,9-hexahydro-1H-pyrazolo[3,4-b]quinoline-3-cyclopropylmethylcarboxamide

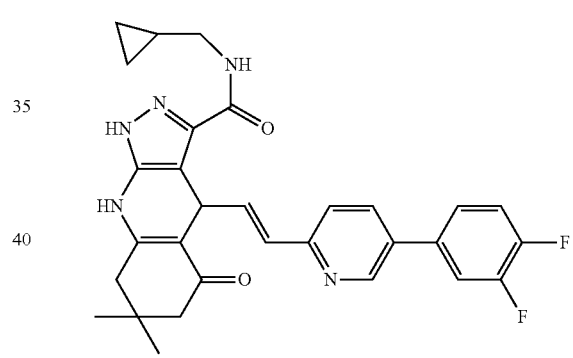

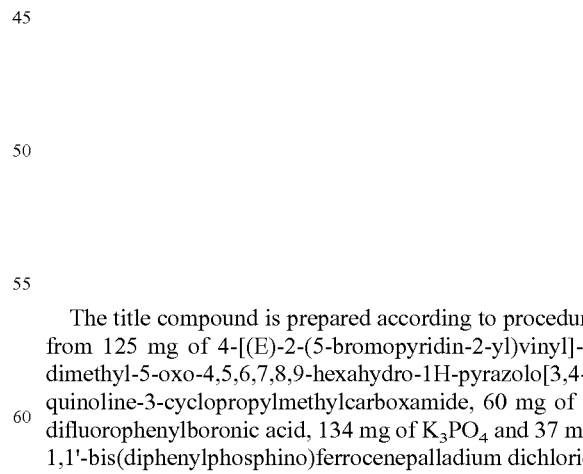

The title compound is prepared according to procedure C from 125 mg of 4-[(E)-2-(5-bromopyridin-2-yl)vinyl]-7,7-dimethyl-5-oxo-4,5,6,7,8,9-hexahydro-1H-pyrazolo[3,4-b]quinoline-3-cyclopropylmethylcarboxamide, 60 mg of 3,4-difluorophenylboronic acid, 134 mg of $K_3PO_4$ and 37 mg of 1,1'-bis(diphenylphosphino)ferrocenepalladium dichloride.

Yield: 39 mg; LC/MS (method J): m/z=530 (M+1); Rt=0.566 min

The compounds in Table 1 below are prepared according to the procedures of the above examples.

TABLE 1
| Example | Structural formula | Rt (from LC/MS) [min] | Mass from LC/MS (m/z) | LC/MS method | Preparation method |
|---|---|---|---|---|---|
| 30 | 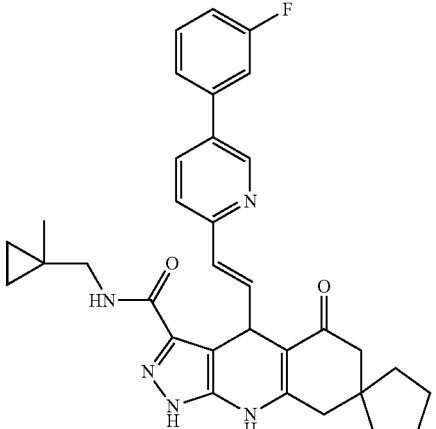 | 0.852 | 552 | J | B |
| 31 | 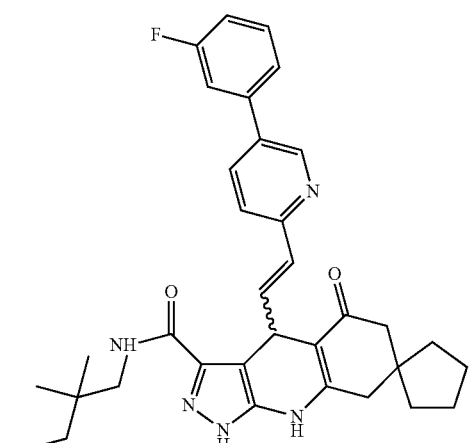 | 21.530 | 570 | B | B |
| 32 | 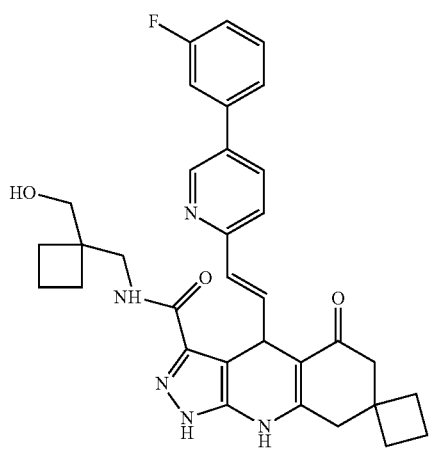 [SMILES: O=C1CC2(CCC2)CC2=C1C(/C=C/c1ccc(-c3cccc(F)c3)cn1)c1c(C(=O)NCC3(CO)CCC3)n[nH]c1N2] | 0.783 | 568 | J | B |

TABLE 1-continued

| Example | Structural formula | Rt (from LC/MS) [min] | Mass from LC/MS (m/z) | LC/MS method | Preparation method |
|---|---|---|---|---|---|
| 33 | | 17.462 | 582 | C | B |
| 34 | | 0.760 | 554 | J | B |
| 35 | | 0.778 | 568 | J | B |

TABLE 1-continued
| Example | Structural formula | Rt (from LC/MS) [min] | Mass from LC/MS (m/z) | LC/MS method | Preparation method |
|---|---|---|---|---|---|
| 36 | 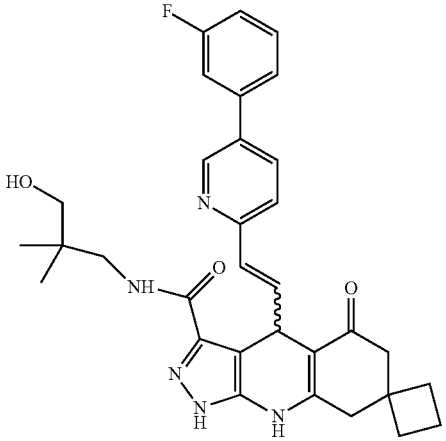 [SMILES: CC(C)(CO)CNC(=O)c1n[nH]c2c1C(C=Cc1ccc(-c3cccc(F)c3)cn1)C1=C(CC3(CCC3)CC1=O)N2] | 15.897 | 556 | C | B |
| 37 | 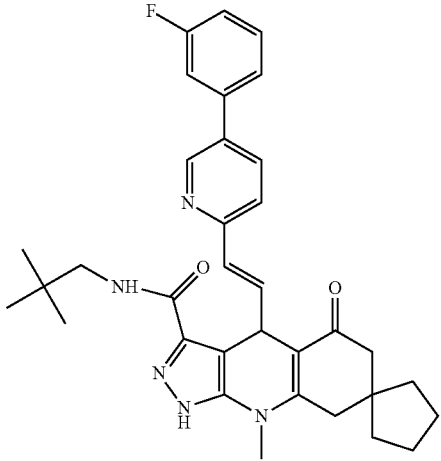 [SMILES: CN1C2=C(C(=O)CC3(CCCC3)C2)C(/C=C/c2ccc(-c3cccc(F)c3)cn2)c2c(C(=O)NCC(C)(C)C)n[nH]c21] | 0.901 | 568 | J | B |
| 38 | 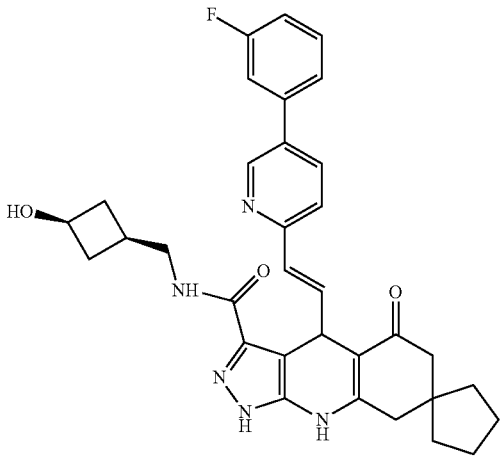 [SMILES: O=C1CC2(CCCC2)CC2=C1C(/C=C/c1ccc(-c3cccc(F)c3)cn1)c1c(C(=O)NC[C@H]3C[C@@H](O)C3)n[nH]c1N2] | 0.767 | 568 | J | B |

TABLE 1-continued

| Example | Structural formula | Rt (from LC/MS) [min] | Mass from LC/MS (m/z) | LC/MS method | Preparation method |
|---|---|---|---|---|---|
| 39 | | 14.236 | 570 | E | B |
| 40 | | 0.814 | 582 | J | B |
| 41 | | 0.838 | 552 | J | A |

TABLE 1-continued

| Example | Structural formula | Rt (from LC/MS) [min] | Mass from LC/MS (m/z) | LC/MS method | Preparation method |
|---|---|---|---|---|---|
| 42 | | 0.811 | 526 | J | A |
| 43 | | 0.764 | 542 | J | B |
| 44 | | 0.769 | 512 | J | B |

TABLE 1-continued
| Example | Structural formula | Rt (from LC/MS) [min] | Mass from LC/MS (m/z) | LC/MS method | Preparation method |
|---|---|---|---|---|---|
| 45 | 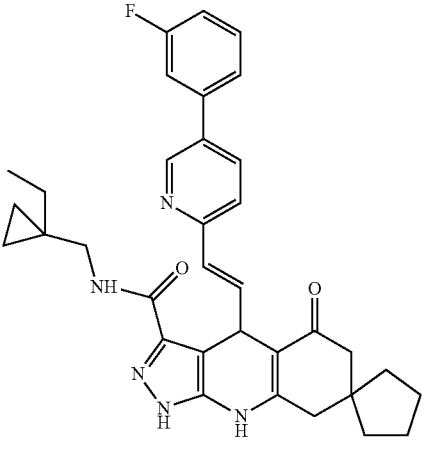 [SMILES: CCC1(CNC(=O)c2n[nH]c3c2C(/C=C/c2ccc(-c4cccc(F)c4)cn2)C2=C(CC4(CCCC4)CC2=O)N3)CC1] | 0.854 | 566 | J | B |
| 46 | 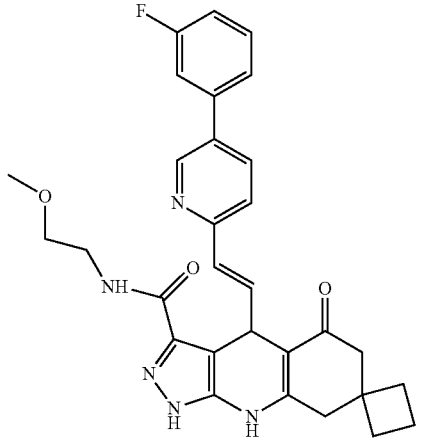 [SMILES: COCCNC(=O)c1n[nH]c2c1C(/C=C/c1ccc(-c3cccc(F)c3)cn1)C1=C(CC3(CCC3)CC1=O)N2] | 0.702 | 528 | J | B |
| 47 | 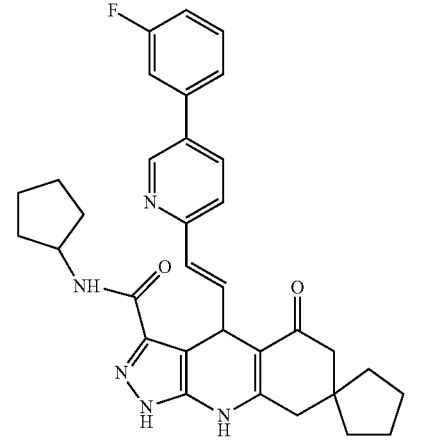 [SMILES: O=C1CC2(CCCC2)CC2=C1C(/C=C/c1ccc(-c3cccc(F)c3)cn1)c1c(C(=O)NC3CCCC3)n[nH]c1N2] | 0.84 | 552 | J | B |

TABLE 1-continued
| Example | Structural formula | Rt (from LC/MS) [min] | Mass from LC/MS (m/z) | LC/MS method | Preparation method |
|---|---|---|---|---|---|
| 48 | 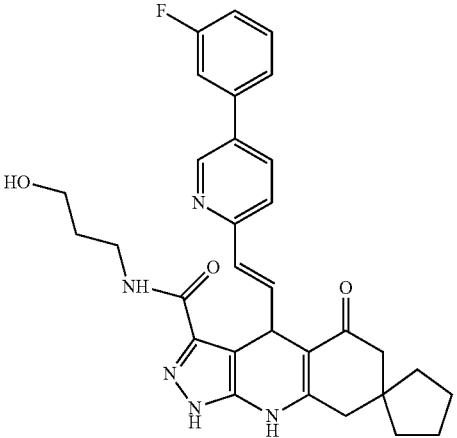 [SMILES: O=C1CC2(CCCC2)CC2=C1C(/C=C/c1ccc(-c3cccc(F)c3)cn1)c1c(C(=O)NCCCO)n[nH]c1N2] | 0.826 | 541 | J | B |
| 49 | 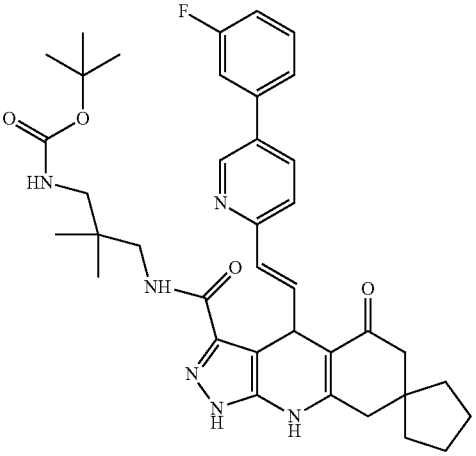 [SMILES: CC(C)(CNC(=O)OC(C)(C)C)CNC(=O)c1n[nH]c2c1C(/C=C/c1ccc(-c3cccc(F)c3)cn1)C1=C(CC3(CCCC3)CC1=O)N2] | 0.926 | 669 | J | B |
| 50 | 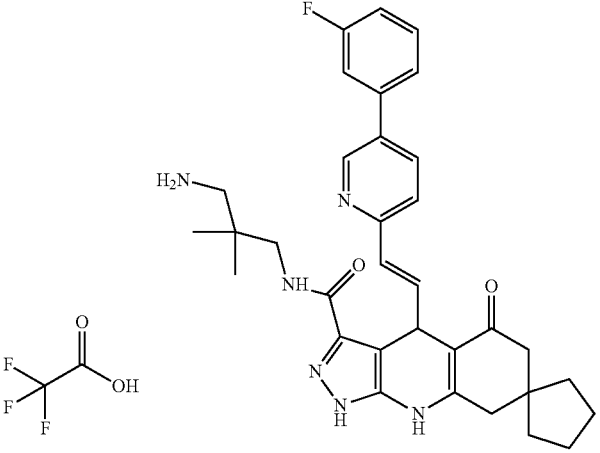 [SMILES: O=C(O)C(F)(F)F ; CC(C)(CN)CNC(=O)c1n[nH]c2c1C(/C=C/c1ccc(-c3cccc(F)c3)cn1)C1=C(CC3(CCCC3)CC1=O)N2] | 0.725 | 569 | J | B |

TABLE 1-continued

| Example | Structural formula | Rt (from LC/MS) [min] | Mass from LC/MS (m/z) | LC/MS method | Preparation method |
|---|---|---|---|---|---|
| 51 | | 0.841 | 582 | J | B |
| 52 | | 0.785 | 582 | J | B |
| 53 | | 0.789 | 568 | J | B |

TABLE 1-continued

| Example | Structural formula | Rt (from LC/MS) [min] | Mass from LC/MS (m/z) | LC/MS method | Preparation method |
|---|---|---|---|---|---|
| 54 | | 0.752 | 568 | J | B |
| 55 | | 0.747 | 582 | J | B |

Pharmacological Examples

PAR1 Determination Method: Inhibition of PAR1-Mediated Platelet Aggregation

The pharmacological testing of the substances took place in platelet aggregation induced by TRAP (thrombin receptor-activating peptide) in 96-well format. For this purpose, blood was taken from healthy volunteers in 20 ml syringes containing 2 ml of 3.13% strength sodium citrate solution. After centrifugation at 150×g for 20 minutes, the platelet-rich plasma (PRP) was separated off and mixed with 1 µl of PGE1 solution (500 µg/ml in ethanol)/ml of PRP. Incubation at RT for 5 minutes was followed by centrifugation at 120×g for 15 minutes to remove the leukocytes. The leukocyte-free PRP was transferred in 5 ml portions into 15 ml PP tubes and centrifuged at 360×g for 15 minutes in order to pellet the platelets. The plasma was then decanted off and the platelet sediment from 5 ml of PRP was resuspended in 1 ml of Tyrode's (120 mM NaCl, 2.6 mM KCl, 12 mM $NaHCO_3$, 0.39 mM $NaH_2PO_4 \times H_2O$, 10 mM HEPES, 0.35% BSA (Bovine Serum Albumin), 5.5 mM glucose, pH 7.4) and adjusted with Tyrode's to a platelet count of $3 \times 10^5$/microliter (µl). 13 µl of this cell suspension were then mixed with 866 µl of 10 mM CaCl2 solution, and 120 µl thereof were pipetted into each well of a 96-well plate containing 15 µl of the substance to be tested. After incubation at RT in the dark for 30 minutes, 15 µl of a TRAP solution (70-100 µM) were added as agonist, and kinetics were recorded at 650 nm in a SpectraMax 340 at 37° C. for 20 minutes while shaking. The areas under the curves of negative control (Tyrode's/DMSO) and positive control (15 µl of agonist/DMSO) were calculated and the difference was fixed as the 100% value. The substances to be tested were pipetted as serial dilutions in duplicate determination, the AUC was likewise determined for each substance concentration, and the % inhibition of the AUC compared with the control was calculated. On the basis of the % inhibition, the $IC_{50}$ was calculated by nonlinear regression analysis according to the 4-parameter equation. Table 2 shows results ($IC_{50}$ values in micromol/l).

TABLE 2

| Compound from example | Inhibition of platelet aggregation $IC_{50}$ [micro M] |
|---|---|
| 8 | 1.88 |
| 10 | 1.39 |
| 13 | 13.44 |

TABLE 2-continued

| Compound from example | Inhibition of platelet aggregation IC$_{50}$ [micro M] |
|---|---|
| 15 | 4.23 |
| diastereomer 1 from example 13 | 5.12 |
| 31 | 0.38 |
| 33 | <0.4 |
| 35 | 0.41 |
| 36 | 0.46 |
| 37 | 0.71 |
| 38 | 0.82 |
| 39 | 0.45 |
| 43 | 1.20 |
| 46 | 1.50 |
| 47 | 1.40 |
| 50 | 0.91 |
| 54 | 0.84 |

What is claimed is:

1. A compound of formula I

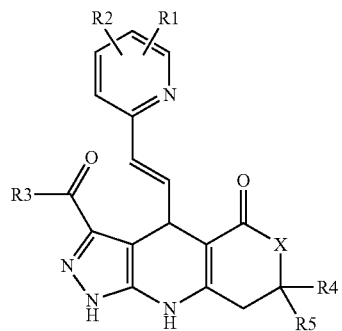

or a physiologically acceptable salt of the compound of formula I, where

R1 and R2 are identical or different and are independently of one another hydrogen, —(C$_1$-C$_6$)-alkyl, —O—(C$_1$-C$_6$)-alkyl, aryl, halogen or hetaryl, where alkyl, aryl and hetaryl are in each case unsubstituted or mono-, di- or trisubstituted independently of one another by F, Cl, Br, CN, —(C$_1$-C$_4$)-alkyl, —O—(C$_1$-C$_4$)-alkyl, or —CF$_3$;

R3 is OH, —O—(C$_1$-C$_8$)-alkyl, —O—(C$_1$-C$_6$)-alkylene-NH—C(O)—O—(C$_1$-C$_4$)-alkyl, —O—(C$_1$-C$_6$)-alkylene-NH$_2$, —NH$_2$, —NH—(C$_1$-C$_8$)-alkyl, —NH—(C$_1$-C$_6$)-alkylenearyl, —NH—(C$_1$-C$_8$)-alkylene-O—(C$_1$-C$_4$)-alkyl, —NH—(C$_1$-C$_8$)-alkyl-OH, —NH—(C$_1$-C$_6$)-alkylene-NH—C(O)—O—(C$_1$-C$_4$)-alkyl, —NH—(C$_1$-C$_6$)-alkylene-NH$_2$, —NH—(C$_0$-C$_6$)-alkylene-(C$_3$-C$_7$)-cycloalkyl, —NH—(C$_0$-C$_6$)-alkylenehetaryl, —N((C$_1$-C$_4$)-alkyl)$_2$, or a cyclic amine which is selected from the group consisting of morpholine, piperazine, piperidine, pyrrolidine and thiomorpholine, and is attached via the nitrogen atom, where aryl, cycloalkyl, and hetaryl are in each case unsubstituted or mono-, di- or trisubstituted independently of one another by F, Cl, —OH, —(C$_1$-C$_4$)-alkyl, —(C$_1$-C$_4$)-alkylene-NH$_2$, —(C$_1$-C$_4$)-alkylene-OH or —O—(C$_1$-C$_4$)-alkyl;

R4 and R5 are identical or different and are independently of one another hydrogen, —(C$_1$-C$_6$)-alkyl or phenyl, or R4 and R5 together with the carbon atom to which they are attached form (C$_3$-C$_7$)-cycloalkyl;

X is a covalent bond, CH$_2$, CH((C$_1$-C$_6$)-alkyl), C((C$_1$-C$_4$)-alkyl)$_2$, or oxygen; and wherein the hetaryl comprises 4 to 15 carbon atoms which are present in one, two or three ring systems connected together, and which comprise, depending on the ring size, one, two, three or four identical or different heteroatoms from the group consisting of oxygen, nitrogen and sulfur, or wherein hetaryl is an oxetanyl residue.

2. The compound of formula I as claimed in claim 1, or a physiologically acceptable salt of the compound of formula I, where R1 and R2 are identical or different and are independently of one another hydrogen, —(C$_1$-C$_6$)-alkyl, —O—(C$_1$-C$_6$)-alkyl, aryl, or halogen, where alkyl, and aryl are in each case unsubstituted or mono-, di- or trisubstituted independently of one another by F, Cl, Br, CN, —(C$_1$-C$_4$)-alkyl, —O—(C$_1$-C$_4$)-alkyl or —CF$_3$;

R3 is —O—(C$_1$-C$_6$)-alkyl, —O—(C$_1$-C$_6$)-alkylene-NH—C(O)—O—(C$_1$-C$_4$)-alkyl, —O—(C$_1$-C$_6$)-alkylene-NH$_2$, —NH—(C$_1$-C$_6$)-alkyl, —NH—(C$_1$-C$_6$)-alkylenearyl, —NH—(C$_1$-C$_6$)-alkylene-(C$_3$-C$_7$)-cycloalkyl, —NH—(C$_1$-C$_6$)-alkylenehetaryl, or —N((C$_1$-C$_4$)-alkyl)$_2$, where aryl, cycloalkyl, and hetaryl are in each case unsubstituted or mono-, di- or trisubstituted independently of one another by F, Cl, —OH, —(C$_1$-C$_4$)-alkylene-NH$_2$, —(C$_1$-C$_4$)-alkylene-OH or —(C$_1$-C$_4$)-alkyl;

R4 and R5 are identical or different and are independently of one another hydrogen or —(C$_1$-C$_6$)-alkyl, or R4 and R5 together with the carbon atom to which they are attached form (C$_3$-C$_6$)-cycloalkyl;

X is a covalent bond, CH$_2$, CH((C$_1$-C$_4$)-alkyl), C((C$_1$-C$_4$)-alkyl)$_2$ or oxygen; and wherein the hetaryl comprises 4 to 15 carbon atoms which are present in one, two or three ring systems connected together, and which comprise, depending on the ring size, one, two, three or four identical or different heteroatoms from the group consisting of oxygen, nitrogen and sulfur, or wherein hetaryl is an oxetanyl residue.

3. The compound as claimed in claim 1 of formula Ia

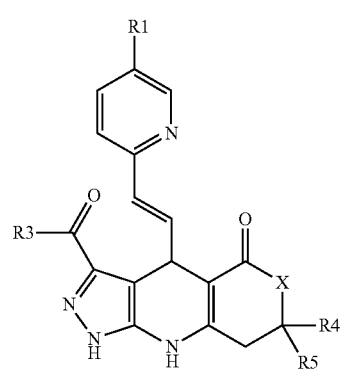

or a physiologically acceptable salt of the compound of the formula Ia, wherein

R1 is hydrogen, —(C$_1$-C$_4$)-alkyl, phenyl, Cl, or Br, and where phenyl is in each case unsubstituted or mono- or disubstituted independently of one another by F, Br, Cl, CN, —(C$_1$-C$_4$)-alkyl, —O—(C$_1$-C$_4$)-alkyl or —CF$_3$;

R3 is OH, —O—(C$_1$-C$_6$)-alkyl, —O—(C$_1$-C$_6$)-alkylene-NH—C(O)—O—(C$_1$-C$_4$)-alkyl, —O—(C$_1$-C$_6$)-alkylene-NH$_2$, —NH—(C$_1$-C$_4$)-alkyl, —NH-benzyl or —NH-methylene-(C$_3$-C$_6$)-cycloalkyl, where cycloalkyl is unsubstituted or monosubstituted by —($C_1$-$C_4$)-alkyl, —($C_1$-$C_4$)-alkylene-$NH_2$ or —$CH_2$—OH;

R4 and R5 are identical or different and are independently of one another hydrogen or —($C_1$-$C_4$)-alkyl, or R4 and R5 together with the carbon atom to which they are attached form cyclopropyl, cyclobutyl, cyclopentyl or cyclohexyl; and X is a covalent bond, $CH_2$, C(($C_1$-$C_4$)-alkyl)$_2$ or oxygen.

4. The compound of formula Ia as claimed in claim 3, or a physiologically acceptable salt of the compound of formula Ia, where R1 is —($C_1$-$C_4$)-alkyl, phenyl, Cl or Br, where phenyl is unsubstituted or mono-, di- or trisubstituted independently of one another by F, Cl, Br, CN, —($C_1$-$C_4$)-alkyl, —O—($C_1$-$C_4$)-alkyl or —$CF_3$;

R3 is OH, —O—($C_1$-$C_4$)-alkyl, —O—($C_1$-$C_6$)-alkylene-NH—C(O)—O—($C_1$-$C_4$)-alkyl, —O—($C_1$-$C_6$)-alkylene-$NH_2$, —NH—($C_1$-$C_3$)-alkyl or —NH-methylene-($C_3$-$C_6$)- cycloalkyl, where cycloalkyl is unsubstituted or monosubstituted by —($C_1$-$C_4$)-alkyl, —($C_1$-$C_4$)-alkylene-$NH_2$ or —$CH_2$—OH;

R4 and R5 are identical or different and are independently of one another hydrogen or —($C_1$-$C_4$)-alkyl, or R4 and R5 together with the carbon atom to which they are attached form cyclobutyl or cyclopentyl;

X is a covalent bond, $CH_2$, C(($C_1$-$C_4$)-alkyl)$_2$ or oxygen.

5. The compound of formula I or Ia as claimed in claims 1 to 4, or a physiologically acceptable salt of the compound of formula I or Ia, where the compound of formula I or Ia is selected from the group consisting of 4-{(E)-2-[5-(3-fluorophenyl)pyridin-2-yl]vinyl}-7,7-dimethyl-5-oxo-4,5,6,7,8,9-hexahydro-1H-pyrazolo[3,4-b]quinoline-3-cyclopropylmethylcarboxamide, 7,7-dimethyl-4-[(E)-2-(6-methylpyridin-2-yl)vinyl]-5-oxo-4,5,6,7,8,9-hexahydro-1 H-pyrazolo[3,4-b]quinoline-3-isopropylcarboxamide, 4-{(E)-2-[5-(3-fluorophenyl)pyridin-2-yl]vinyl}-7,7-dimethyl-5-oxo-4,5,6,7,8,9-hexahydro-1H-pyrazolo[3,4-b]quinoline-3-isopropylcarboxamide, 4-{(E)-2-[5-(3-fluorophenyl)pyridin-2-yl]vinyl}-6,6-dimethyl-5-oxo-4,5,6,7,8,9-hexahydro-1H-pyrazolo[3,4-b]quinoline-3-cyclopropylmethylcarboxamide, 4-{(E)-2-[5-(3-fluorophenyl)pyridin-2-yl]vinyl}-7-isopropyl-5-oxo-4,5,6,7,8,9-hexahydro-1H-pyrazolo[3,4-b]quinoline-3-cyclopropylmethylcarboxamide, 4-[(E)-2-(5-bromopyridin-2-yl)vinyl]-7,7-dimethyl-5-oxo-4,5,6,7,8,9-hexahydro-1H-pyrazolo[3,4-b]quinoline-3-cyclopropylmethylcarboxamide, 4-[(E)-2-(5-bromopyridin-2-yl)vinyl]-7,7-dimethyl-5-oxo-4,5,6,7,8,9-hexahydro-1H-pyrazolo[3,4-b]quinoline-3-isopropylcarboxamide, 4-{(E)-2-[5-(3-fluorophenyl)pyridin-2-yl]vinyl}-7-methyl-5-oxo-4,5,6,7,8,9-hexahydro-1H-pyrazolo[3,4-b]quinoline-3-isopropylcarboxamide, 4-{(E)-2-[5-(3-fluorophenyl)pyridin-2-yl]vinyl}-7-methyl-5-oxo-4,5,6,7,8,9-hexahydro-1H-pyrazolo[3,4-b]quinoline-3-cyclopropylmethylcarboxamide, ethyl 4-{(E)-2-[5-(3-fluorophenyl)pyridin-2-yl]vinyl}-7,7-dimethyl-5-oxo-4,5,6,7,8,9-hexahydro-1H-pyrazolo[3,4-b]quinoline-3-carboxylate, and 4-{(E)-2-[5-(3-fluorophenyl)pyridin-2-yl]vinyl}-7,7-dimethyl-5-oxo-4,5,6,7,8,9-hexahydro-1H-pyrazolo[3,4-b]quinoline-3-(2,2-dimethylpropyl)carboxamide.

6. A pharmaceutical composition having an effective amount of at least one compound of the formula I or a physiologically acceptable salt thereof as claimed in claim 1 and a pharmaceutically suitable and physiologically acceptable carrier.

7. A pharmaceutical composition comprising an effective amount of at least one compound or a physiologically acceptable salt thereof as claimed in claim 5 and a pharmaceutically suitable and physiologically acceptable carrier.

8. A process for preparing a compound of formula I or a physiologically acceptable salt thereof as claimed in claim 1, which comprises a) reacting a compound of the formula II,

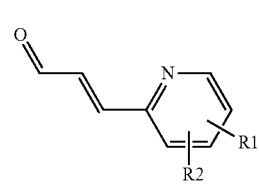

where the radicals R1, R2 are as defined in claim 1 for the compound of formula, with a compound of the formula III and a compound of the formula IV,

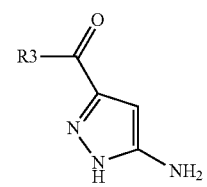

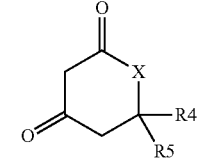

where the radicals R1, R2 are as defined in formula I in claim 1, in the presence of a suitable solvent or solvent mixture at 20° C. to 120° C. to give a compound of the formula I; or b) reacting a compound of formula V,

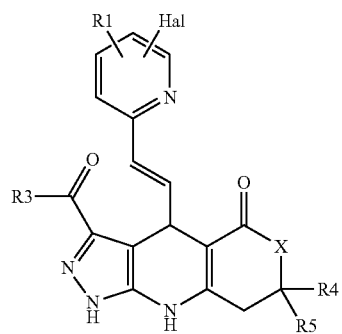

where the radicals X, R1, R3, R4 and R5 are as defined in formula I in claim 1, and Hal is chlorine, bromine, iodine or triflate, with a compound of the formula R2-B(OH)2 in the presence of a base and of a suitable metal catalyst in a suitable solvent or solvent mixture to give a compound of formula I or II; or c) reacting a compound of the formula I in which X has the meaning of NH with a suitable alkylating agent in the presence of a base and in a suitable inert solvent at room temperature or at elevated temperature to give a compound of the formula I in which X has the meaning of N—R6 and R6 is —(C1-C6)-alkyl, —(C1-C6)-alkylene-(C3-C7)-cycloalkyl or —(C1-C6)-alkylenearyl; or d) converting a compound of formula I in which R3 is —OH, —O-aryl or —O—(C1-C6)-alkyl and R1, R2, R4, R5 and X are as defined in formula I in claim 1 by conventional processes into a compound of the formula I in which R3 is —NH2, —NH—(C1-C6)-alkyl, —NH—(C1-C6)-alkylenearyl, —NH—(C1-C6)-alkylene-(C3-C7)-cycloalkyl, —NH—(C1-C6)-alkylenehetaryl, —N((C1-C4)-alkyl)2 or a cyclic amine which is selected from the group consisting of hexamethyleneimine, morpholine, piperazine, piperidine, pyrrolidine and thiomorpholine, and is attached via the nitrogen atom, where aryl, hetaryl and cyclic amine are in each case unsubstituted or mono-, di- or trisubstituted independently of one another by F, Cl, —OH, —(C1-C4)-alkyl, —O—(C1-C4)-alkyl, aryl or hetaryl; or e) fractionating the compound of formula I which has been prepared by processes a) to d), or a suitable precursor of the compound of the formula I which, owing to its chemical structure, occurs in enantiomeric or diastereomeric forms, by salt formation with enantiomerically pure acids or bases, chromatography on chiral stationary phases or derivatization by means of chiral enantiomerically pure compounds such as amino acids, separation of the diastereomers obtained in this way, and elimination of the chiral auxiliary groups, into the pure enantiomers or diastereomers; or f) either isolating the compound of formula I prepared by processes a) to e) in free form or liberating it from a non-physiologically acceptable salt or, in the case where acidic or basic groups are present, converting it into a physiologically acceptable salt.

\* \* \* \* \*